(12) United States Patent
Schottek

(10) Patent No.: US 7,034,173 B2
(45) Date of Patent: Apr. 25, 2006

(54) CHEMICAL PRODUCTS SUITED FOR USE AS CO-CATALYSTS, METHOD FOR THE PREPARATION THEREOF AND THEIR USE IN CATALYST SYSTEMS FOR PRODUCING POLYOLEFINS

(75) Inventor: Jörg Schottek, Frankfurt (DE)

(73) Assignee: Basell Polyolefine GmbH, (DE)

( * ) Notice: Subject to any disclaimer, the term of this patent is extended or adjusted under 35 U.S.C. 154(b) by 626 days.

(21) Appl. No.: 10/276,782

(22) PCT Filed: May 19, 2001

(86) PCT No.: PCT/EP01/05752

§ 371 (c)(1),
(2), (4) Date: Nov. 20, 2002

(87) PCT Pub. No.: WO01/90112

PCT Pub. Date: Nov. 29, 2001

(65) Prior Publication Data

US 2003/0144434 A1   Jul. 31, 2003

(30) Foreign Application Priority Data

May 24, 2000  (DE) ............................... 100 25 412

(51) Int. Cl.
*C07F 5/00* (2006.01)
*C07F 5/06* (2006.01)

(52) U.S. Cl. ...................... 556/179; 556/182; 502/152; 502/414; 502/202; 526/165; 526/133; 526/154; 526/155

(58) Field of Classification Search ................ 556/179, 556/182; 502/152, 414, 202; 526/133, 165, 526/154, 155
See application file for complete search history.

(56) References Cited

U.S. PATENT DOCUMENTS

| | | | |
|---|---|---|---|
| 5,384,299 A | 1/1995 | Turner et al. | 502/155 |
| 5,414,064 A | 5/1995 | Lux et al. | 526/215 |
| 5,565,534 A | 10/1996 | Aulbach et al. | 526/160 |
| 5,710,297 A | 1/1998 | Weller et al. | 556/11 |
| 5,770,753 A | 6/1998 | Küber et al. | 556/11 |
| 5,786,432 A | 7/1998 | Küber et al. | 526/127 |
| 5,792,819 A | 8/1998 | Erker et al. | 522/134 |
| 5,840,644 A | 11/1998 | Küber et al. | 502/117 |
| 5,840,948 A | 11/1998 | Rohrmann et al. | 556/11 |
| 5,852,142 A | 12/1998 | Rohrmann et al. | 526/127 |
| 5,929,264 A | 7/1999 | Rohrmann et al. | 556/11 |
| 5,990,254 A | 11/1999 | Weller et al. | 526/160 |
| 6,002,032 A | 12/1999 | Erker et al. | 556/11 |
| 6,051,522 A | 4/2000 | Rohrmann et al. | 502/103 |
| 6,051,727 A | 4/2000 | Küber et al. | 556/11 |
| 6,242,544 B1 | 6/2001 | Küber et al. | 526/127 |
| 6,255,506 B1 | 7/2001 | Küber et al. | 556/11 |

FOREIGN PATENT DOCUMENTS

| | | |
|---|---|---|
| DE | 3 543 360 | 6/1987 |
| EP | 0 107 127 | 5/1984 |
| EP | 0 129 368 | 12/1984 |
| EP | 0 416 815 | 3/1991 |
| EP | 0 426 637 | 5/1991 |
| EP | 0 520 732 | 12/1992 |

(Continued)

OTHER PUBLICATIONS

Yang et al., "'Cation-like' Homogeneous Olefin Polymerization Catalysts Based upon Zirconocene Alkyls and Tris (pentafluorophenyl)borane", *J. Am. Chem. Soc.*, 113, pp. 3623-3625 (1991).

(Continued)

*Primary Examiner*—Caixia Lu
(74) *Attorney, Agent, or Firm*—Connolly Bove Lodge & Hutz

(57) ABSTRACT

The invention relates to chemical products which are suited for use as co-catalysts and which can be obtained by reacting a compound of formula (I), $M^1R^1R^2(R^3)_m$ with a compound of formula (II), $(R^4X)_q\text{-}(G)^*(M^2R^5R^6)_g$. In formula (I), $R^1$, $R^2$ and $R^3$ are the same or different and represent a hydrogen atom, $C_1$–$C_{20}$ alkyl, $C_1$–$C_{20}$ alkyl halide, $C_6$–$C_{20}$ aryl, $C_6$–$C_{20}$ aryl halide, $C_7$–$C_{40}$ arylalkyl, $C_7$–$C_{40}$ arylalkyl halide, $C_7$–$C_{40}$ alkylaryl or $C_7$–$C_{40}$ alkylaryl halide; $M^1$ represents an element of the second or third main group of the periodic table of elements, and; m equals 0 or 1, whereby m is equal to 1 when $M^1$ represents an element of the third main group, and m is equal to 0 when $M^1$ represents an element of the second main group. In formula (II), substituents $R^4X$, which contain hetero atoms, is located on a base body G, and: groups $R^4$ are the same or different and represent hydrogen, $C_1$–$C_{20}$ alkyl, $C_1$–$C_{20}$ alkyl halide, $C_6$–$C_{20}$ aryl, $C_6$–$C_{20}$ aryl halide, $C_7$–$C_{40}$ arylalkyl, $C_7$–$C_{40}$ arylalkyl halide, $C_7$–$C_{40}$ akylaryl or $C_7$–$C_{40}$ alkylaryl halide; X represents an element of the fourth, fifth or sixth main group of the periodic table of elements; G represents at least bivalent $C_1$–$C_{20}$ alkylene, $C_1$–$C_{20}$ alkylene halide, $C_1$–$C_{10}$ alkylenoxy, $C_6$–$C_{40}$ arylene, $C_6$–$C_{40}$ arylene halide, $C_6$–$C_{40}$ arylenoxy, $C_7$–$C_{40}$ arylalkylene, $C_7$–$C_{40}$ arylalkylene halide, $C_7$–$C_{40}$ alkylarylene, $C_7$–$C_{40}$ alkylarylene halide; $M^2$ represents an element of the fourth, fifth or sixth main group of the periodic table of elements; $R^5$ and $R^6$, independent of one another, are the same or different and represent a hydrogen atom, $C_1$–$C_{20}$ alkyl, $C_1$–$C_{10}$ alkoxy, $C_2$–$C_{10}$ alkenyl, $C_7$–$C_{20}$ arylalkyl, $C_7$–$C_{20}$ alkylaryl, $C_6$–$C_{10}$ aryloxy, $C_1$–$C_{10}$ alkyl halide; q is a whole number ranging from 2 to 100, and; g is a whole number ranging from 1 to 100. The invention also relates to a method for preparing the inventive chemical products, and to their use in catalyst systems for producing polyolefins.

7 Claims, No Drawings

FOREIGN PATENT DOCUMENTS

| | | |
|---|---|---|
| EP | 0 545 304 | 9/1993 |
| EP | 0 558 158 | 9/1993 |
| EP | 0 561 476 | 9/1993 |
| EP | 0 561 479 | 9/1993 |
| EP | 0 576 970 | 1/1994 |
| EP | 0 632 063 | 1/1995 |
| EP | 0 636 636 | 2/1995 |
| EP | 0 659 758 | 6/1995 |
| EP | 0 661 300 | 7/1995 |
| EP | 0 687 682 | 12/1995 |
| JP | 03 271295 | 12/1991 |
| WO | 91/09882 | 7/1991 |
| WO | 96/04319 | 2/1996 |
| WO | 98/22486 | 5/1998 |
| WO | 99/30819 | 6/1999 |
| WO | 99/30820 | 6/1999 |
| WO | 99/30821 | 6/1999 |
| WO | 00/64906 | 11/2000 |

OTHER PUBLICATIONS

Brintziner et al., "Stereospezifische Olefinpolymerisation mit chiralen Metalloenkatalysatoren", *Angew. Che*, 107, pp. 1255-1283 (1995).

Johnson et al., "New Pd(II)- and Ni(II)-Based Catalysts for Polymerization of Ethylene and -Olefins", *J. Am. Chem. Soc.*, 117, pp. 6414-6415 (1995).

Derwent Abstract of JP 09-278817 (Oct. 28, 1997).

Scollard et al., "Polymerization of -Olefins by Chelating Diamide Complexes of Titanium", *Macromolecules*, 29, pp. 5241-5243 (1996).

Johnson et al., "Copolymerization of Ethylene and Propylene with Functionalized Vinyl Monomers by Palladium(II) Catalysts", *J. Am. Chem Soc.*, 118, pp. 267-268 (1996).

Scollard et al., "Living Polymerization of -Olefins by Chelating Diamide Complexes of Titanium", *J. Am. Chem. Soc.*, 118, pp. 10008-10009 (1996).

Britovsek et al., "Novel olefin polymerization catalysts based on iron and cobalt". *Chem. Commun.*, pp. 849-850 (1998).

Small et al., "Highly Active Iron and Cobalt Catalysts for the Polymerization of Ethylene", *J. Am. Chem Soc.*, 120, pp. 4049-4050 (1998).

CHEMICAL PRODUCTS SUITED FOR USE AS CO-CATALYSTS, METHOD FOR THE PREPARATION THEREOF AND THEIR USE IN CATALYST SYSTEMS FOR PRODUCING POLYOLEFINS

The present invention relates to chemical products suitable as cocatalysts, to processes for preparing them and to their use in catalyst systems for preparing polyolefins. In particular, the invention relates to chemical products which are electrically neutral and in combination with an organic transition metal compound can form a catalyst system which can advantageously be used for the polymerization of olefins. Here, the use of aluminoxanes such as methylaluminoxane (MAO) as cocatalyst can be dispensed with while nevertheless achieving a high catalyst activity and good polymer morphology.

The role of cationic complexes in Ziegler-Natta polymerization using metallocenes is generally recognized (H. H. Brintzinger, D. Fischer, R. Mülhaupt, R. Rieger, R. Waymouth, Angew. Chem. 1995, 107, 1255–1283).

MAO as effective cocatalyst has the disadvantage that it has to be used in a large excess. Although modified MAO cocatalysts have been described, for example in WO99/30819, WO99/30820, WO99/30821 and JP-09-278817 A1, these systems display unsatisfactory polymerization activities and have to be used in a large excess.

The preparation of cationic transition metal alkyl complexes opens the way to MAO-free catalysts having comparable activity, in which the cocatalyst can be used in an almost stoichiometric amount.

The synthesis of "cation-like" metallocene polymerization catalysts is described in J. Am. Chem. Soc. 1991, 113, 3623. A process for preparing salts of the formula $LMX^+ XA^-$ according to the above-described principle is described in EP-A-0 520 732.

EP-A-0 558 158 describes zwitterionic catalyst systems which are prepared from dialkyl-metallocene compounds and salts of the formula $[R_3NH]^+ [B(C_6H_5)_4]^-$. Reaction of such a salt with, for example, $Cp_2ZrMe_2$ results in protolysis with elimination of methane to give a methyl-zirconocene cation as intermediate. This reacts via C—H activation to form the zwitterion $Cp_2Zr^+$—(m-$C_6H_4$)—$BPh_3^-$. In this zwitterion, the Zr atom is covalently bound to a carbon atom of the phenyl ring and is stabilized by a agostic hydrogen bonds.

U.S. Pat. No. 5,348,299 describes zwitterionic catalyst systems which are prepared from dialkyl-metallocene compounds and salts of the formula $[R_3NH]^+ [B(C_6F_5)_4]^-$ by protolysis. The C—H-activation as subsequent reaction does not occur. In EP-A-0 426 637, the Lewis-acid $CPh_3^+$ cation is used for abstraction of the methyl group from the metal center. $B(C_6F_5)_4^-$ functions as weakly coordinating anion.

To enable metallocene catalysts to be utilized industrially, the catalyst system has to be made heterogeneous in order to ensure appropriate morphology of the resulting polymer. The application of cationic metallocene catalysts based on the above-mentioned borate anions to a support is described in WO 91/09882. Here, the catalyst system is formed by applying a dialkyl-metallocene compound and a Brönsted-acid, quaternary ammonium compound having a noncoordinating anion such as tetrakispentafluorophenyl borate to an inorganic support. The support material is modified beforehand using a trialkylaluminum compound.

A disadvantage of this method of application to a support is that only a small part of the metallocene used is fixed to the support material by physisorbtion. When the catalyst system is introduced into the reactor, the metallocene can easily be leached from the support surface. This leads to a partly homogeneous polymerization, resulting in an unsatisfactory morphology of the polymer. WO 96/04319 describes a catalyst system in which the cocatalyst is covalently bound to the support material. However, this catalyst system has a low polymerization activity and, in addition, the high sensitivity of the supported cationic metallocene catalysts can lead to problems during introduction into the polymerization system.

It is an object of the present invention to provide a chemical product which can be used as cocatalyst in catalyst systems and displays the positive properties of MAO and can also be physisorbed on or covalently bound to a support material. The catalyst system formed therefrom should be able to be activated either before the introduction into the reactor or only in the polymerization autoclave.

We have found that this object is achieved by chemical products which are suitable as cocatalysts and are obtainable by reacting a compound of the formula (I),

$$M^1R^1R^2(R^3)_m \qquad (I),$$

where $R^1$, $R^2$, $R^3$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl, $M^1$ is an element of main group II or III of the Periodic Table of the Elements and m is 0 or 1, with m being 1 when $M^1$ is an element of main group III and m being 0 when $M^1$ is an element of main group II, with a compound of the formula (II),

$$(R^4X)_q\text{-}(G)^*(M^2R^5R^6)_g \qquad (II),$$

in which heteroatom-containing substituents $R^4X$ are located on a parent moiety G, where $R^4$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl, $C_7$–$C_{40}$-haloalkylaryl, X is an element of main group IV, V or VI of the Periodic Table of the Elements, G is at least divalent $C_1$–$C_{20}$-alkylene, $C_1$–$C_{20}$-haloalkylene, $C_1$–$C_{10}$-alkyleneoxy, $C_6$–$C_{40}$-arylene, $C_6$–$C_{40}$-haloarylene, $C_6$–$C_{40}$-aryleneoxy, $C_7$–$C_{40}$-arylalkylene, $C_7$–$C_{40}$-haloarylalkylene, $C_7$–$C_{40}$-alkylarylene, $C_7$–$C_{40}$-haloalkylarylene, $M^2$ is an element of main group IV, V or VI of the Periodic Table of the Elements, $R^5$, $R^6$ are identical or different and are each hydrogen, $C_1$–$C_{20}$-alkyl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, q is an integer from 2 to 100 and g is an integer from 1 to 100.

The present invention also provides a process for preparing this chemical product by reacting a compound of the formula (I),

$$M^1R^1R^2(R^3)_m \qquad (I),$$

where $R^1$, $R^2$, $R^3$ are identical or different and are each hydrogen, $C_1$–$C_{20}$-alkyl, $C_1$–$C_{20}$-haloalkyl, $C_6$–$C_{20}$-aryl, $C_6$–$C_{20}$- haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl, $M^1$ is an element of main group II or III of the Periodic Table of the Elements and m is 0 or 1, with m being 1 when $M^1$ is an element of main group III and m being 0 when $M^1$ is an element of main group II, with a compound of the formula (II),

(II), in which heteroatom-containing substituents $R^4X$ are located on a parent moiety G, where $R^4$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl, $C_7$–$C_{40}$-haloalkylaryl, x is an element of main group IV, V or VI of the Periodic Table of the Elements, G is at least divalent $C_1$–$C_{20}$-alkylene, $C_1$–$C_{20}$-haloalkylene, $C_1$–$C_{10}$-alkyleneoxy, $C_6$–$C_{40}$-arylene, $C_6$–$C_{40}$-haloarylene, $C_6$–$C_{40}$-aryleneoxy, $C_7$–$C_{40}$-arylalkylene, $C_7$–$C_{40}$-haloarylalkylene, $C_7$–$C_{40}$-alkylarylene, $C_7$–$C_{40}$-haloalkylarylene, $M^2$ is an element of main group IV, V or VI of the Periodic Table of the Elements, $R^5$, $R^6$ are identical or different and are each hydrogen, $C_1$–$C_{20}$-alkyl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl, q is an integer from 2 to 100 and g is an integer from 1 to 100.

The chemical products of the present invention preferably comprise groups of the formula (III),

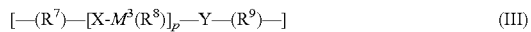

(III)

where $R^7$, $R^8$ are identical or different and are each a hydrogen atom, a halogen atom, a boron-free $C_1$–$C_{40}$ group such as $C_1$–$C_{20}$-alkyl, $C_1$–$C_{40}$-haloalkyl, $C_1$–$C_{10}$-alkoxy, $C_6$–$C_{40}$-aryl $C_6$–$C_{40}$-haloaryl, $C_6$–$C_{20}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl or an $Si(R^{13})_3$ group, $R^9$ is identical to or different from $R^7$ and $R^8$ and is a hydrogen atom or a $C_1$–$C_{40}$ group such as $C_1$–$C_{20}$-alkyl, $C_1$–$C_{20}$-haloalkyl, $C_1$–$C_{10}$-alkoxy, $C_6$–$C_{40}$-aryl, $C_6$–$C_{40}$-haloaryl, $C_6$–$C_{40}$-aryloxy, $C_7$–$C_{40}$-arylalkyl, $C_7$–$C_{40}$-haloarylalkyl, $C_7$–$C_{40}$-alkylaryl, $C_7$–$C_{40}$-haloalkylaryl, (preferably partially halogenated or fully halogenated $C_1$–$C_{20}$-haloalkyl or $C_6$–$C_{40}$-haloaryl halogenated by chlorine or fluorine, particularly preferably $C_6$–$C_{40}$-haloaryl halogenated by fluorine), X are identical or different and are each an element of group IV, V or VI of the Periodic Table of the Elements or an NH group, Y are identical or different and are each an element of group IV, V or VI of the Periodic Table of the Elements or an NH group and $M^3$ is an element of group IIIa of the Periodic Table of the Elements.

The compounds of the formula (III) can form dimers, trimers or higher oligomers having linear or cage-like structures among one another. In general, k compounds of the formula (III) are associated as a result of Lewis acid-base interactions, where k is a natural number from 1 to 100.

Particular preference is given to novel chemical compounds of the formula (III) in which $R^7$, $R^8$ are identical or different and are each $C_1$–$C_{20}$-alkyl, $C_1$–$C_{40}$-haloalkyl, $C_6$–$C_{40}$-aryl, $C_6$–$C_{40}$-haloaryl, $C_7$–$C_{40}$-arylalkyl, $C_7$–$C_{40}$-haloarylalkyl, $C_7$–$C_{40}$-alkylaryl, $C_7$–$C_{40}$-haloalkylaryl $R^9$ can be identical to or different from $R^7$ and $R^8$ and is $C_6$–$C_{40}$-aryl, $C_6$–$C_{40}$-haloaryl, $C_7$–$C_{40}$-arylalkyl, $C_7$–$C_{40}$-haloarylalkyl, $C_7$–$C_{40}$-alkylaryl, $C_7$–$C_{40}$-haloalkylaryl, preferably partially halogenated or fully halogenated $C_1$–$C_{20}$-haloalkyl or $C_6$–$C_{40}$-haloaryl halogenated by chlorine or fluorine, particularly preferably $C_6$–$C_{40}$-haloaryl halogenated by fluorine, X are identical or different and are each an element of main group V or VIa of the Periodic Table of the Elements, preferably an oxygen or sulfur atom or an NH group, Y are identical or different and are each an element of main group V or VIa of the Periodic Table of the Elements, preferably an oxygen or sulfur atom or an NH group, $M^3$ is boron or aluminum, preferably aluminum, and k is a natural number from 1 to 100.

Very particular preference is given to novel chemical compounds of the formula (III), in which $R^7$, $R^8$ are identical or different and are each a $C_1$–$C_{20}$-alkyl or $C_1$–$C_{20}$-haloalkyl group, e.g. methyl, ethyl, isopropyl, isobutyl $R^9$ is different from $R^7$ and $R^8$ and is partially halogenated or fully halogenated $C_6$–$C_{40}$-haloaryl, $C_7$–$C_{40}$-haloarylalky, $C_7$–$C_{40}$-haloalkylaryl, preferably a fluorinated group such as pentafluorophenoxy, pentachlorophenoxy, halogenated or partially halogenated biphenyloxy groups, X is an oxygen atom, Y is an oxygen atom, $M^3$ is aluminum, k is a natural number from 1 to 100.

$R^7$ and $R^8$ are particularly preferably phenyl, methyl, ethyl, isopropyl, butyl, tolyl, biphenyl or 2,3-dimethylphenyl.

$R^9$ is particularly preferably a halogenated or perhalogenated $C_6$–$C_{30}$-aryl group, for example a halogenated or partially halogenated biphenyl such as octafluorobiphenyl, heptafluorobiphenyl, hexafluorobiphenyl.

According to the present invention, preference is given to using compounds of the formula (I) in which $R^1$, $R^2$ and $R^3$ are $C_1$–$C_6$-alkyl groups. $R^1$, $R^2$ and $R^3$ are particularly preferably $C_1$–$C_4$-alkyl groups. In the formula (I), $M^1$ is preferably an element of main group III of the Periodic Table of the Elements, in particular boron or aluminum. Very particular preference is given to aluminum.

Particularly preferred aluminum compounds of the formula (I) are trimethylaluminum, triethylaluminum, triisopropylaluminum, trihexylaluminum, trioctylaluminum, tri-n-butylaluminum, tri-n-propylaluminum and triisoprenylaluminum. Among these, trimethylaluminum, triethylaluminum and triisopropylaluminum are particularly preferred.

Particularly preferred boron compounds of the formula (I) are triethylborane and boranes having branched alkyl radicals.

In preferred compounds of the formula (II), the parent moiety G is preferably a partially or fully halogenated $C_1$–$C_{20}$-haloalkylene or $C_6$–$C_{40}$-haloarylene, where chlorine and/or fluorine are used as halogen. G is particularly preferably a partially or fully fluorinated $C_6$–$C_{40}$-arylene.

In formula (II), X is preferably oxygen, nitrogen or sulfur, particularly preferably oxygen or sulfur and very particularly preferably oxygen. Furthermore, $R^4$ in formula (II) is preferably hydrogen or $C_1$–$C_{20}$-alkyl, particularly preferably hydrogen.

In formula (II), the integer q preferably assumes values in the range from 1 to 40, particularly preferably from 1 to 10. In a very particularly preferred embodiment of the invention, q is 2.

In the compounds of the formula (II), $M^2$ is preferably silicon, oxygen, nitrogen or sulfur, in particular oxygen. $R^5$, $R^6$ are preferably hydrogen or $C_1$–$C_{20}$-alkyl, very particularly preferably hydrogen. The integer g preferably assumes values in the range from 0 to 10, in particular from 1 to 5 and particularly preferably 1 or 2. In a very particularly preferred embodiment of the invention, g is 1.

In the compounds of the formula (II), $(M^2R^5R^6)_g$ is preferably water or an alcohol. Particular preference is given to water, methanol, ethanol and branched alcohols. Very particular preference is given to using water.

Particularly preferred compounds of the formula (II) in which G is a partially or fully fluorinated $C_6$–$C_{40}$-arylene bear, as substituents $R^4X$, from 2 to 40, preferably from 2 to 20, very particularly preferably from two to eight, hydroxyl groups.

Nonlimiting examples of chemical compounds of the formula (II) are:
4,4'-dihydroxyoctafluorobiphenyl*(s*$H_2O$),
4,3'-dihydroxyoctafluorobiphenyl*(s*$H_2O$),
4,5'-dihydroxyoctafluorobiphenyl*(s*$H_2O$),
4,6'-dihydroxyoctafluorobiphenyl*(s*$H_2O$),
4,7'-dihydroxyoctafluorobiphenyl*(s*$H_2O$),
4,8'-dihydroxyoctafluorobiphenyl*(s*$H_2O$),
1,2-dihydroxyoctafluorobiphenyl*(s*$H_2O$),
1,3-dihydroxyoctafluorobiphenyl*(s*$H_2O$),
4,4'-dihydroxyheptafluorobiphenyl*(s*$H_2O$),
4,3'-dihydroxyheptafluorobiphenyl*(s*$H_2O$),
4,5'-dihydroxyheptafluorobiphenyl*(s*$H_2O$),
4,6'-dihydroxyheptafluorobiphenyl*(s*$H_2O$),
4,7'-dihydroxyheptafluorobiphenyl*(s*$H_2O$),
4,8'-dihydroxyheptafluorobiphenyl*(s*$H_2O$),
1,2-dihydroxyheptafluorobiphenyl*(s*$H_2O$),
1,3-dihydroxyheptafluorobiphenyl*(s*$H_2O$),
4,4'-dihydroxyhexafluorobiphenyl*(s*$H_2O$),
4,3'-dihydroxyhexafluorobiphenyl*(s*$H_2O$),
4,5'-dihydroxyhexafluorobiphenyl*(s*$H_2O$),
4,6'-dihydroxyhexafluorobiphenyl*(s*$H_2O$),
4,7'-dihydroxyhexafluorobiphenyl*(s*$H_2O$),
4,8'-dihydroxyhexafluorobiphenyl*(s*$H_2O$),
1,2-dihydroxyhexafluorobiphenyl*(s*$H_2O$),
1,3-dihydroxyhexafluorobiphenyl*(s*$H_2O$),
4,4'-dihydroxypentafluorobiphenyl*(s*$H_2O$),
4,3'-dihydroxypentafluorobiphenyl*(s*$H_2O$),
4,5'-dihydroxypentafluorobiphenyl*(s*$H_2O$),
4,6'-dihydroxypentafluorobiphenyl*(s*$H_2O$),
4,7'-dihydroxypentafluorobiphenyl*(s*$H_2O$),
4,8'-dihydroxypentafluorobiphenyl*(s*$H_2O$),
1,2-dihydroxypentafluorobiphenyl*(s*$H_2O$),
1,3-dihydroxypentafluorobiphenyl*(s*$H_2O$),
4,4'-dihydroxyoctachlorobiphenyl*(s*$H_2O$),
4,3'-dihydroxyoctachlorobiphenyl*(s*$H_2O$),
4,5'-dihydroxyoctachlorobiphenyl*(s*$H_2O$),
4,6'-dihydroxyoctachlorobiphenyl*(s*$H_2O$),
4,7'-dihydroxyoctachlorobiphenyl*(s*$H_2O$),
4,8'-dihydroxyoctachlorobiphenyl*(s*$H_2O$),
1,2-dihydroxyoctachlorobiphenyl*(s*$H_2O$),
1,3-dihydroxyoctachlorobiphenyl*(s*$H_2O$),
4,4'-dihydroxyheptachlorobiphenyl*(s*$H_2O$),
4,3'-dihydroxyheptachlorobiphenyl*(s*$H_2O$),
4,5'-dihydroxyheptachlorobiphenyl*(s*$H_2O$),
4,6'-dihydroxyheptachlorobiphenyl*(s*$H_2O$),
4,7'-dihydroxyheptachlorobiphenyl*(s*$H_2O$),
4,8'-dihydroxyheptachlorobiphenyl*(s*$H_2O$),
1,2-dihydroxyheptachlorobiphenyl*(s*$H_2O$),
1,3-dihydroxyheptachlorobiphenyl*(s*$H_2O$),
4,4'-dihydroxyhexachlorobiphenyl*(s*$H_2O$),
4,3'-dihydroxyhexachlorobiphenyl*(s*$H_2O$),
4,5'-dihydroxyhexachlorobiphenyl*(s*$H_2O$),
4,6'-dihydroxyhexachlorobiphenyl*(s*$H_2O$),
4,7'-dihydroxyhexachlorobiphenyl*(s*$H_2O$),
4,8'-dihydroxyhexachlorobiphenyl*(s*$H_2O$),
1,2-dihydroxyhexachlorobiphenyl*(s*$H_2O$),
1,3-dihydroxyhexachlorobiphenyl*(s*$H_2O$),
4,4'-dihydroxypentachlorobiphenyl*(s*$H_2O$),
4,3'-dihydroxypentachlorobiphenyl*(s*$H_2O$),
4,5'-dihydroxypentachlorobiphenyl*(s*$H_2O$),
4,6'-dihydroxypentachlorobiphenyl*(s*$H_2O$),
4,7'-dihydroxypentachlorobiphenyl*(s*$H_2O$),
4,8'-dihydroxypentachlorobiphenyl*(s*$H_2O$),
1,2-dihydroxypentachlorobiphenyl*(s*$H_2O$),
1,3-dihydroxypentachlorobiphenyl*(s*$H_2O$),
1,8-dihydroxyhexafluoronaphthalene*(s*$H_2O$),
1,7-dihydroxyhexafluoronaphthalene*(s*$H_2O$),
1,6-dihydroxyhexafluoronaphthalene*(s*$H_2O$),
1,7-dihydroxyhexafluoronaphthalene*(s*$H_2O$),
1,5-dihydroxyhexafluoronaphthalene*(s*$H_2O$),
1,4-dihydroxyhexafluoronaphthalene*(s*$H_2O$),
1,3-dihydroxyhexafluoronaphthalene*(s*$H_2O$),
1,2-dihydroxyhexafluoronaphthalene*(s*$H_2O$),
1,8-dihydroxyhexachloronaphthalene*(s*$H_2O$),
1,7-dihydroxyhexachloronaphthalene*(s*$H_2O$),
1,6-dihydroxyhexachloronaphthalene*(s*$H_2O$),
1,7-dihydroxyhexachloronaphthalene*(s*$H_2O$),
1,5-dihydroxyhexachloronaphthalene*(s*$H_2O$),
1,4-dihydroxyhexachloronaphthalene*(s*$H_2O$),
1,3-dihydroxyhexachloronaphthalene*(s*$H_2O$),
1,2-dihydroxyhexachloronaphthalene*(s*$H_2O$),
1,8-dihydroxypentafluoronaphthalene*(s*$H_2O$),
1,7-dihydroxypentafluoronaphthalene*(s*$H_2O$),
1,6-dihydroxypentafluoronaphthalene*(s*$H_2O$),
1,7-dihydroxypentafluoronaphthalene*(s*$H_2O$),
1,5-dihydroxypentafluoronaphthalene*(s*$H_2O$),
1,4-dihydroxypentafluoronaphthalene*(s*$H_2O$),
1,3-dihydroxypentafluoronaphthalene*(s*$H_2O$),
1,2-dihydroxypentafluoronaphthalene*(s*$H_2O$),
1,8-dihydroxytetrakisfluoronaphthalene*(s*$H_2O$),
1,7-dihydroxytetrakisfluoronaphthalene*(s*$H_2O$),
1,6-dihydroxytetrakisfluoronaphthalene*(s*$H_2O$),
1,7-dihydroxytetrakisfluoronaphthalene*(s*$H_2O$),
1,5-dihydroxytetrakisfluoronaphthalene*(s*$H_2O$),
1,4-dihydroxytetrakisfluoronaphthalene*(s*$H_2O$),
1,3-dihydroxytetrakisfluoronaphthalene*(s*$H_2O$),
1,2-dihydroxytetrakisfluoronaphthalene*(s*$H_2O$),
1,2-dihydroxy-3,4,5,6,7,8,9,10,11,12-decafluoroterphenyl*(s*$H_2O$), 1,3-dihydroxy-2,4,5,6,7,8,9,10,11,12-decafluoroterphenyl*(s*$H_2O$),
1,4-dihydroxy-2,3,5,6,7,8,9,10,11,12-decafluoroterphenyl*(s*$H_2O$), 1,5-dihydroxy-2,3,4,6,7,8,9,10,11,12-decafluoroterphenyl*(S*$H_2O$),
1,6-dihydroxy-2,3,4,5,7,8,9,10,11,12-decafluoroterphenyl*(s*$H_2O$), 1,7-dihydroxy-2,3,4,5,6,8,9,10,11,12-decafluoroterphenyl*(s*$H_2O$), 1,8-dihydroxy-2,3,4,5,6,7,9,10,11,12-decafluoroterphenyl*(s*H$_2$O), 1,9-dihydroxy-2,3,4,5,6,7,8,10,11,12-decafluoroterphenyl*(s*H$_2$O),
1,10-dihydroxy-2,3,4,5,6,7,8,9,11,12-decafluoroterphenyl*(s*H$_2$O), 1,11-dihydroxy-2,3,4,5,6,7,8,9,10,12-decafluoroterphenyl*(s*H$_2$O),
1,12-dihydroxy-2,3,4,5,6,7,8,9,10,11,12-decafluoroterphenyl*(s*H$_2$O), 1,9-dihydrokynonafluoroanthracene*(s*H$_2$O),
1,2-dihydroxynonafluoroanthracene*(s*H$_2$O),
1,3-dihydroxynonafluoroanthracene*(s*H$_2$O),
1,4-dihydroxynonafluoroanthracene*(s*H$_2$O),
1,5-dihydroxynonafluoroanthracene*(s*H$_2$O),
1,6-dihydroxynonafluoroanthracene*(s*H$_2$O),
1,7-dihydroxynonafluoroanthracene*(s*H$_2$O),
1,8-dihydroxynonafluoroanthracene*(s*H$_2$O),
1,9-dihydroxynonachloroanthracene*(s*H$_2$O),
1,3-dihydroxynonachloroanthracene*(s*H$_2$O),
1,4-dihydroxynonachloroanthracene*(s*H$_2$O),
1,5-dihydroxynonachloroanthracene*(s*H$_2$O),
1,6-dihydroxynonachloroanthracene*(s*H$_2$O),
1,7-dihydroxynonachloroanthracene*(s*H$_2$O),
1,8-dihydroxynonachloroanthracene*(s*H$_2$O),
1,9-dihydroxyoctafluoroanthracene*(s*H$_2$O),
1,2-dihydroxyoctafluoroanthracene*(s*H$_2$O),
1,3-dihydroxyoctafluoroanthracene*(s*H$_2$O),
1,4-dihydroxyoctafluoroanthracene*(s*H$_2$O),
1,5-dihydroxyoctafluoroanthracene*(s*H$_2$O),
1,6-dihydroxyoctafluoroanthracene*(s*H$_2$O),
1,7-dihydroxyoctafluoroanthracene*(s*H$_2$O),
1,8-dihydroxyoctafluoroanthracene*(s*H$_2$O),
1,9-dihydroxyheptafluoroanthracene*(s*H$_2$O),
1,2-dihydroxyheptafluoroanthracene*(s*H$_2$O),
1,3-dihydroxyheptafluoroanthracene*(s*H$_2$O),
1,4-dihydroxyheptafluoroanthracene*(s*H$_2$O),
1,5-dihydroxyheptafluoroanthracene*(s*H$_2$O),
1,6-dihydroxyheptafluoroanthracene*(s*H$_2$O),
1,7-dihydroxyheptafluoroanthracene*(s*H$_2$O),
1,8-dihydroxyheptafluoroanthracene*(s*H$_2$O),
1,9-dihydroxyhexafluoroanthracene*(s*H$_2$O),
1,2-dihydroxyhexafluoroanthracene*(s*H$_2$O),
1,3-dihydroxyhexafluoroanthracene*(s*H$_2$O),
1,4-dihydroxyhexafluoroanthracene*(s*H$_2$O),
1,5-dihydroxyhexafluoroanthracene*(s*H$_2$O),
1,6-dihydroxyhexafluoroanthracene*(s*H$_2$O),
1,7-dihydroxyhexafluoroanthracene*(s*H$_2$O),
1,8-dihydroxyhexafluoroanthracene*(s*H$_2$O),
1,9-dihydroxynonafluorophenanthrene*(s*H$_2$O),
1,2-dihydroxynonafluorophenanthrene*(s*H$_2$O),
1,3-dihydroxynonafluorophenanthrene*(s*H$_2$O),
1,4-dihydroxynonafluorophenanthrene*(s*H$_2$O),
1,5-dihydroxynonafluorophenanthrene*(s*H$_2$O),
1,6-dihydroxynonafluorophenanthrene*(s*H$_2$O),
1,7-dihydroxynonafluorophenanthrene*(s*H$_2$O),
1,8-dihydroxynonafluorophenanthrene*(s*H$_2$O),
1,9-dihydroxynonachlorophenanthrene*(s*H$_2$O),
1,3-dihydroxynonachlorophenanthrene*(s*H$_2$O),
1,4-dihydroxynonachlorophenanthrene*(s*H$_2$O),
1,5-dihydroxynonachlorophenanthrene*(s*H$_2$O),
1,6-dihydroxynonachlorophenanthrene*(s*H$_2$O),
1,7-dihydroxynonachlorophenanthrene*(s*H$_2$O),
1,8-dihydroxynonachlorophenanthrene*(s*H$_2$O),
1,9-dihydroxyoctafluorophenanthrene*(s*H$_2$O),
1,2-dihydroxyoctafluorophenanthrene*(s*H$_2$O),
1,3-dihydroxyoctafluorophenanthrene*(s*H$_2$O),
1,4-dihydroxyoctafluorophenanthrene*(s*H$_2$O),
1,5-dihydroxyoctafluorophenanthrene*(s*H$_2$O),
1,6-dihydroxyoctafluorophenanthrene*(s*H$_2$O),
1,7-dihydroxyoctafluorophenanthrene*(s*H$_2$O),
1,8-dihydroxyoctafluorophenanthrene*(s*H$_2$O),
1,9-dihydroxyheptafluorophenanthrene*(s*H$_2$O),
1,2-dihydroxyheptafluorophenanthrene*(s*H$_2$O),
1,3-dihydroxyheptafluorophenanthrene*(s*H$_2$O),
1,4-dihydroxyheptafluorophenanthrene*(s*H$_2$O),
1,5-dihydroxyheptafluorophenanthrene*(s*H$_2$O),
1,6-dihydroxyheptafluorophenanthrene*(s*H$_2$O),
1,7-dihydroxyheptafluorophenanthrene*(s*H$_2$O),
1,8-dihydroxyheptafluorophenanthrene*(s*H$_2$O),
1,9-dihydroxyhexafluorophenanthrene*(s*H$_2$O),
1,2-dihydroxyhexafluorophenanthrene*(s*H$_2$O),
1,3-dihydroxyhexafluorophenanthrene*(s*H$_2$O),
1,4-dihydroxyhexafluorophenanthrene*(s*H$_2$O),
1,5-dihydroxyhexafluorophenanthrene*(s*H$_2$O),
1,6-dihydroxyhexafluorophenanthrene*(s*H$_2$O),
1,7-dihydroxyhexafluorophenanthrene*(s*H$_2$O),
1,8-dihydroxyhexafluorophenanthrene*(S*H$_2$O),
4,5,4'-trihydroxyheptafluorobiphenyl*(s*H$_2$O),
4,5,3'-trihydroxyheptafluorobiphenyl*(s*H$_2$O),
4,5,5'-trihydroxyheptafluorobiphenyl*(s*H$_2$O),
4,5,6'-trihydroxyheptafluorobiphenyl*(s*H$_2$O),
3,4,5',7'-tetrahydroxyhexafluorobiphenyl*(s*H$_2$O),
3,4,6',8'-tetrahydroxyhexafluorobiphenyl*(s*H$_2$O),
3,5,5',7'-tetrahydroxyhexafluorobiphenyl*(s*H$_2$O),
3,5,3',5'-tetrahydroxyhexafluorobiphenyl*(s*H$_2$O),
where s is preferably 1, 2, 3, 4, 5, 6, 7, 8, 9, 10, 11, 12, 13, 14, 15, 16, 17, 18, 19, 20.

The present invention also provides a supported catalyst system in which the chemical products obtainable by reacting compounds of the formula (I) with compounds of the formula (II) are used as cocatalysts, and provides a process for preparing this catalyst system. In addition, the invention provides a process for preparing polyolefins by polymerization in the presence of the catalyst systems of the present invention.

The reaction according to the present invention of compounds of the formula (I) with compounds of the formula (II) to give the chemical product of the present invention is generally carried out using the following procedure.

Firstly, one or more compounds of the formula (I) can be placed in a reaction vessel. The compounds can either be dissolved or suspended in a solvent or can be present as such. Suitable solvents are aliphatic or aromatic hydrocarbons such as n-pentane, isopentane, n-hexane, n-heptane, cyclohexane, isododecane, n-octane, n-nonane, n-decane, petroleum ether, toluene, benzene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene, etc. and also ethers such as diethyl ether, methyl tert-butyl ether, dimethoxyethane, diisopropyl ether, di-n-butyl ether, anisole or mixtures thereof. Among these, particular preference is given to aromatic hydrocarbons, in particular toluene, o-xylene, m-xylene, p-xylene, 1,2,3-trimethylbenzene, 1,2,4-trimethylbenzene, 1,2,5-trimethylbenzene and 1,3,5-trimethylbenzene. The compounds of the formula (I) and any solvents used are generally placed in the reaction vessel at from −100° C. to 300° C., preferably from −80° C. to 200° C., particularly preferably from 20° C. to 150° C. The compound of the formula (I) is advantageously present in a liquid phase.

One or more compounds of the formula (II) can subsequently be added. The compounds of the formula (II) can likewise be dissolved or suspended in a solvent or be added as such. Suitable solvents are those described above; preference is given to using the same solvent. The addition can be carried out over a period of from 1 minute to 96 hours. The addition is preferably carried out within a period of from 10 minutes to 8 hours. The temperature of the initial charge during the addition is in the range from −100° C. to 200° C., preferably from −80° C. to 150° C., particularly preferably from 20° C. to 150° C. The temperature is generally selected so that at least one reactant is present in a liquid phase. The subsequent reaction temperature is preferably in a range from 20° C. to 150° C. The reaction can be carried out at atmospheric pressure or superatmospheric pressure, although the latter requires appropriate reactors. The molar ratio in which the compounds of the formula (I) and those of the formula (II) are combined is generally in the range from 1:1000 to 1:0.01, based on the amount of $M^1$ in the compounds of the formula (I).

The molar ratio of compounds of the formula (I) to those of the formula (II) is preferably from 1:100 to 1:0.1, based on the amount of $M^1$ in the compounds of the formula (I). Particular preference is given to stoichiometric reaction of the compounds of the formulae (I) and (II). The molar ratio here depends on the number g of (($M^2R^5R^6$)) groups. The figures given here assume a value of 1 for g. In the case of higher values of g, a correspondingly smaller amount of compound (II) can be used.

The present invention also provides a process for preparing the products suitable as cocatalysts, in which compounds of the formula (I) are reacted with compounds of the formula (II).

The present invention additionally provides a catalyst system which preferably comprises
A) at least one organic transition metal compound,
B) if desired, at least one main group alkyl,
C) if desired, at least one support component and
D) at least one chemical product which is obtainable by reacting compounds of the formula (I) with compounds of the formula (II) and preferably comprises compounds of the formula (III).

As organic transition metal compound A), preference is given to using metallocene compounds. These can be, for example, bridged or unbridged biscyclopentadienyl complexes as are described, for example, in EP-A-0 129 368, EP-A-0 561 479, EP-A-0 545 304 and EP-A-0 576 970, monocyclopentadienyl complexes such as bridged amidocyclopentadienyl complexes as described, for example, in EP-A-0 416 815, multinuclear cyclopentadienyl complexes as described, for example, in EP-A-0 632 063, π-ligand-substituted tetrahydropentalenes as described, for example, in EP-A-0 659 758 or π-ligand-substituted tetrahydroindenes as described, for example, in EP-A-0 661 300. It is also possible to use organic metal compounds in which the complexing ligand contains no cyclopentadienyl units. Examples are diamine complexes of elements of transition groups III and IV of the Periodic Table of the Elements, as are described, for example, in D. H. McConville, et al., Macromolecules, 1996, 29, 5241 and D. H. McConville, et al., J. Am. Chem. Soc., 1996, 118, 10008. Diimine complexes of elements of transition group VIII of the Periodic Table of the Elements (e.g. $Ni^{2+}$ or $Pd^{2+}$ complexes) as described by Brookhart et al., J. Am. Chem. Soc. 1995, 117, 6414 and Brookhart et al., J. Am. Chem. Soc. 1996, 118, 267 can also be used. Furthermore, 2,6-bis(imino)pyridyl complexes of metals of transition group VIII of the Periodic Table of the Elements (e.g. $Co^{2+}$ or $Fe^{2+}$ complexes) as described in Brookhart et al., J. Am. Chem. Soc. 1998, 120, 4049 and Gibson et al., Chem. Commun. 1998, 849 can be used. It is also possible to use metallocene compounds whose complexing ligand contains heterocycles. Examples of such compounds are described in WO 98/22486.

Preferred metallocene compounds are unbridged or bridged compounds of the formula (IV),

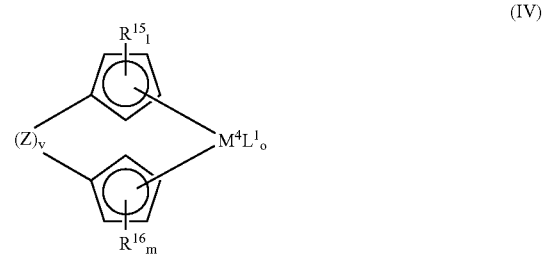

where
$M^4$ is a metal of transition group III, IV, V or VI of the Periodic Table of the Elements, in particular Ti, Zr or Hf,
$R^{15}$ are identical or different and are each a hydrogen atom or $Si(R^{17})_3$, where $R^{17}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{20}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^{15}$ is a $C_1$–$C_{30}$ group, preferably $C_1$–$C_{25}$-alkyl, such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^{15}$ may be joined in such a way that the radicals $R^{15}$ and the atoms of the cyclopentadienyl ring which connect them form a $C_4$–$C_{24}$-ring system which may in turn be substituted,
$R^{16}$ are identical or different and are each a hydrogen atom or $Si(R^{18})_3$, where $R^{18}$ are identical or different and are each a hydrogen atom or a $C_1$–$C_{40}$ group, preferably $C_1$–$C_{20}$-alkyl, $C_1$–$C_{10}$-fluoroalkyl, $C_1$–$C_{10}$-alkoxy, $C_6$–$C_{14}$-aryl, $C_6$–$C_{10}$-fluoroaryl, $C_6$–$C_{10}$-aryloxy, $C_2$–$C_{10}$-alkenyl, $C_7$–$C_{40}$-arylalkyl, $C_7$–$C_{40}$-alkylaryl or $C_8$–$C_{40}$-arylalkenyl, or $R^{16}$ is a $C_1$–$C_{30}$ group, preferably $C_1$–$C_{25}$-alkyl such as methyl, ethyl, tert-butyl, cyclohexyl or octyl, $C_2$–$C_{25}$-alkenyl, $C_3$–$C_{15}$-alkylalkenyl, $C_6$–$C_{24}$-aryl, $C_5$–$C_{24}$-heteroaryl, $C_5$–$C_{24}$-alkylheteroaryl, $C_7$–$C_{30}$-arylalkyl, $C_7$–$C_{30}$-alkylaryl, fluorinated $C_1$–$C_{25}$-alkyl, fluorinated $C_6$–$C_{24}$-aryl, fluorinated $C_7$–$C_{30}$-arylalkyl, fluorinated $C_7$–$C_{30}$-alkylaryl or $C_1$–$C_{12}$-alkoxy, or two or more radicals $R^{16}$ may be joined in such a way that the radicals $R^{16}$ and the atoms of the cyclopentadienyl ring which connect them form a $C_4$–$C_{24}$-ring system which may in turn be substituted,
l is 5 when v=0, and l is 4 when v=1,
m is 5 when v=0, and m is 4 when v=1,
$L^1$ may be identical or different and are each a hydrogen atom, a $C_1$–$C_{10}$-hydrocarbon group such as $C_1$–$C_{10}$-alkyl or $C_6$–$C_{10}$-aryl, a halogen atom or $OR^{19}$, $SR^{19}$, $OSi(R^{19})_3$, $Si(R^{19})_3$, $P(R^{19})_2$ or $N(R^{19})_2$, where $R^{19}$ is a halogen atom, a $C_1$–$C_{10}$-alkyl group, a halogenated $C_1$–$C_{10}$-alkyl group, a $C_6$–$C_{20}$-aryl group or a halogenated $C_6$–$C_{20}$-aryl group, or $L^1$ is a toluenesulfonyl, trifluoroacetyl, trifluoroacetoxyl, trifluoromethanesulfonyl, nonafluorobutanesulfonyl or 2,2,2-trifluoroethanesulfonyl group,
o is an integer from 1 to 4, preferably 2, Z is a bridging structural element between the two cyclopentadienyl rings and v is 0 or 1.

Examples of Z are $M^5R^{20}R^{21}$ groups, where $M^5$ is carbon, silicon, germanium, boron or tin and $R^{20}$ and $R^{21}$ are identical or different and are each a $C_1$–$C_{20}$-hydrocarbon-containing group such as $C_1$–$C_{10}$-alkyl, $C_6$–$C_{14}$-aryl or trimethylsilyl. Z is preferably $CH_2$, $CH_2CH_2$, $CH(CH_3)CH_2$, $CH(C_4H_9)C(CH_3)_2$, $C(CH_3)_2$, $(CH_3)_2Si$, $(CH_3)_2Ge$, $(CH_3)_2Sn$, $(C_6H_5)_2Si$, $(C_6H_5)(CH_3)Si$, $(C_6H_5)_2Ge$, $(CH_3)_3Si$—$Si(CH_3)(C_6H_5)_2Sn$, $(CH_2)_4S_1$, $CH_2Si(CH_3)2$, MeSi—Si(Me)$_3$, o-$C_6H_4$ or 2,2'-$(C_6H_4)_2$, or a 1,2-(1-methylethanediyl), 1,2-(1,1-dimethylethanediyl) or 1,2(1,2-dimethylethanediyl) bridge. It is also possible for Z together with one or more radicals $R^{15}$ and/or $R^{16}$ to form a monocyclic or polycyclic ring system.

Preference is given to chiral bridged metallocene compounds of the formula (IV), particularly those in which v is 1 and one or both cyclopentadienyl rings are substituted so that they form an indenyl ring. The indenyl ring is preferably substituted, particularly in the 2 position, the 4 position, the 2,4,5 positions, the 2,4,6 positions, the 2,4,7 positions or the 2,4,5,6 positions, by $C_1$–$C_{20}$ groups such as $C_1$–$C_{10}$-alkyl or $C_6$–$C_{20}$-aryl, where two or more substituents of the indenyl ring may also together form a ring system.

Chiral bridged metallocene compounds of the formula (IV) can be used as pure racemic or pure meso compounds. However, it is also possible to use mixtures of a racemic compound and a meso compound.

Examples of metallocene compounds are:
dimethylsilanediylbis(indenyl)zirconium dichloride
dimethylsilanediylbis(4-naphthylindenyl)zirconium dichloride
dimethylsilanediylbis (2-methylbenzoindenyl) zirconium dichloride
dimethylsilanediylbis(2-methylindenyl)zirconium dichloride
dimethylsilanediylbis(2-methyl-4-(1-naphthyl)indenyl)zirconium dichloride
dimethylsilanediylbis(2-methyl-4-(2-naphthyl)indenyl)zirconium dichloride
dimethylsilanediylbis(2-methyl-4-phenylindenyl)zirconium dichloride
dimethylsilanediylbis(2-methyl-4-tert-butylindenyl)zirconium dichloride
dimethylsilanediylbis(2-methyl-4-isopropylindenyl)zirconium dichloride
dimethylsilanediylbis(2-methyl-4-ethylindenyl)zirconium dichloride
dimethylsilanediylbis(2-methyl-4-α-acenaphthindenyl)zirconium dichloride
dimethylsilanediylbis(2,4-dimethylindenyl)zirconium dichloride
dimethylsilanediylbis(2-ethylindenyl)zirconium dichloride
dimethylsilanediylbis(2-ethyl-4-ethylindenyl)zirconium dichloride
dimethylsilanediylbis(2-ethyl-4-phenylindenyl)zirconium dichloride
dimethylsilanediybis(2-methyl-4,5-benzoindenyl)zirconium dichloride
dimethylsilanediylbis(2-methyl-4,6-diisopropylindenyl)zirconium dichloride
dimethylsilanediylbis(2-methyl-4,5-diisopropylindenyl)zirconium dichloride
dimethylsilanediylbis(2,4,6-trimethylindenyl)zirconium dichloride
dimethylsilanediylbis(2,5,6-trimethylindenyl)zirconium dichloride
dimethylsilanediylbis(2,4,7-trimethylindenyl)zirconium dichloride
dimethylsilanediylbis(2-methyl-5-isobutylindenyl)zirconium dichloride
dimethylsilanediylbis(2-methyl-5-t-butylindenyl)zirconium dichloride
methyl(phenyl)silanediylbis(2-methyl-4-phenylindenyl)zirconium dichloride
methyl(phenyl)silanediylbis(2-methyl-4,6-diisopropylindenyl)zirconium dichloride
methyl(phenyl)silanediylbis(2-methyl-4-isopropylindenyl)zirconium dichloride
methyl(phenyl)silanediylbis(2-methyl-4,5-benzoindenyl)zirconium dichloride
methyl(phenyl)silanediylbis(2-methyl-4,5-(methylbenzo)indenyl)zirconium dichloride
methyl(phenyl)silanediylbis(2-methyl-4,5-(tetramethylbenzo)indenyl)zirconium dichloride
methyl(phenyl)silanediylbis(2-methyl-4-α-acenaphthindenyl)zirconium dichloride
methyl(phenyl)silanediylbis(2-methylindenyl)zirconium dichloride
methyl(phenyl)silanediylbis(2-methyl-5-isobutylindenyl)zirconium dichloride
1,2-ethanediylbis(2-methyl-4-phenylindenyl)zirconium dichloride
1,4-butanediylbis(2-methyl-4-phenylindenyl)zirconium dichloride
1,2-ethanediylbis(2-methyl-4,6-diisopropylindenyl)zirconium dichloride
1,4-butanediylbis(2-methyl-4-isopropylindenyl)zirconium dichloride
1,4-butanediylbis(2-methyl-4,5-benzoindenyl)zirconium dichloride
1,2-ethanediylbis(2-methyl-4,5-benzoindenyl)zirconium dichloride
1,2-ethanediylbis(2,4,7-trimethylindenyl)zirconium dichloride
1,2-ethanediylbis(2-methylindenyl)zirconium dichloride
1,4-butanediylbis (2-methylindenyl) zirconium dichloride
[4-($\eta^5$-cyclopentadienyl)-4,6,6-trimethyl-($\eta^5$-4,5-tetrahydropentalene)]dichlorozirconium
[4-($\eta^5$-3'-trimethylsilylcyclopentadienyl)-4,6,6-trimethyl-($\eta^5$-4,5-tetrahydropentalene)]dichlorozirconium
[4-($\eta^5$-3'-isopropylcyclopentadienyl)-4,6,6-trimethyl-($\eta^5$-4,5-tetrahydropentalene)]didhlorozirconium
[4-($\eta^5$-cyclopentadienyl)-4,7,7-trimethyl-($\eta^5$-4,5,6,7-tetrahydroindenyl))dichlorotitanium
[4-($\eta^5$-cyclopentadienyl)-4,7,7-trimethyl-($\eta^5$-4,5,6,7-tetrahydroindenyl)]dichlorozirconium
[4-($\eta^5$-cyclopentadienyl)-4,7,7-trimethyl-($\eta^5$-4,5,6,7-tetrahydroindenyl)]dichlorohafnium
[4-($\eta^5$-3'-tert-butylcyclopentadienyl)-4,7,7-trimethyl-($\eta^5$-4,5,6,7-tetrahydroindenyl)]dichlorotitanium
4-($\eta^5$-3'-isopropylcyclopentadienyl)-4,7,7-trimethyl-($\eta^5$-4,5,6,7-tetrahydroindenyl)]dichlorotitanium
4-($\eta^5$-3'-methylcyclopentadienyl)-4,7,7-trimethyl-($\eta^5$-4,5,6,7-tetrahydroindenyl)]dichlorotitanium
4-($\eta^5$-3'-trimethylsilylcyclopentadienyl)-2-trimethylsilyl-4,7,7-trimethyl-($\eta^5$-4,5,6,7-tetrahydroindenyl))dichlorotitanium
4-($\eta^5$-3'-tert-butylcyclopentadienyl)-4,7,7-trimethyl-($\eta^5$-4,5,6,7-tetrahydroindenyl)]dichlorozirconium
(tert-butylamido)(tetramethyl-$\eta^5$-cyclopentadienyl)dimethylsilyldichlorotitanium
(tert-butylamido)(tetramethyl-$\eta^5$-cyclopentadienyl)-1,2-ethanediyldichlorotitanium (methylamido)(tetramethyl-$\eta^5$-cyclopentadienyl)dimethyl-silyldichlorotitanium
(methylamido)(tetramethyl-$\eta^5$-cyclopentadienyl)-1,2-ethanediyldichlorotitanium
(tert-butylamido)-(2,4-dimethyl-2,4-pentadien-1-yl)-dimethylsilyl dichlorotitanium
bis-(cyclopentadienyl)zirconium dichloride
bis-(n-butylcyclopentadienyl)zirconium dichloride
bis-(1,3-dimethylcyclopentadienyl)zirconium dichloride
tetrachloro-[1-[bis($\eta^5$-1H-inden-1-ylidene)methylsilyl]-3-$\eta^5$-cyclopenta-2,4-dien-1-ylidene)-3-$\eta^5$-9H-fluoren-9-ylidene)butane]-dizirconium
tetrachloro-[2-[bis($\eta^5$-2-methyl-1H-inden-1-ylidene)methoxysilyl]-5-($\eta^5$-2,3,4,5-tetramethylcyclopenta-2,4-dien-1-ylidene)-5-($\eta^5$-9H-fluoren-9-ylidene)hexane]dizirconium
tetrachloro-[1-[bis($\eta^5$-1H-inden-1-ylidene)methylsilyl]-6-($\eta^5$-cyclopenta-2,4-dien-1-ylidene)-6-($\eta^5$-9H-fluoren-9-ylidene)-3-oxaheptane]dizirconium
dimethylsilanediylbis(2-methyl-4-(tert-butylphenylindenyl)zirconium dichloride
dimethylsilanediylbis(2-methyl-4-(4-methylphenylindenyl)zirconium dichloride
dimethylsilanediylbis(2-methyl-4-(4-ethylphenylindenyl)zirconium dichloride
dimethylsilanediylbis(2-methyl-4-(4-trifluormethylphenylindenyl)zirconium dichloride
dimethylsilanediylbis(2-methyl-4-(4-methoxyphenylindenyl)zirconium dichloride
dimethylsilanediylbis(2-ethyl-4-(4-tert-butylphenylindenyl)zirconium dichloride
dimethylsilanediylbis (2-ethyl-4-(4-methylphenylindenyl)zirconium dichloride
dimethylsilanediylbis(2-ethyl-4-(4-ethylphenylindenyl)zirconium dichloride
dimethylsilanediylbis(2-ethyl-4-(4-trifluoromethyl-phenylindenyl)zirconium dichloride
dimethylsilanediylbis(2-ethyl-4-(4-methoxyphenylindenyl)zirconium dichloride
dimethylsilanediylbis(2-methyl-4-(4-tert-butylphenylindenyl)dimethylzirconium
dimethylsilanediylbis(2-methyl-4-(4-methylphenylindenyl)dimethylzirconium
dimethylsilanediylbis(2-methyl-4-(4-ethylphenylindenyl)dimethylzirconium
dimethylsilanediylbis(2-methyl-4-(4-trifluoromethylphenylindenyl) dimethylzirconium
dimethylsilahediylbis(2-methyl-4-(4-methoxyphenylindenyl)dimethyl zirconium
dimethylsilanediylbis(2-ethyl-4-(4-tert-butylphenylindenyl) dimethylzirconium
dimethylsilanediylbis(2-ethyl-4-(4-methylphenylindenyl) dimethylzirconium
dimethylsilanediylbis(2-ethyl-4-(4-ethylphenylindenyl)diethylzirconium
dimethylsilanediylbis(2-ethyl-4-(4-trifluoromethylphenylindenyl)dimethylzirconium
dimethylsilanediylbis(2-ethyl-4-(4-methoxyphenylindenyl) dimethylzirconium
dimethylsilanediylbis(2-methyl-4-(4'-tert-butylphenyl)indenyl)zirconium dichloride
dimethylsilanediylbis(2-methyl-4-(4'-tert-butylphenyl)indenyl)hafnium dichloride
dimethylsilanediylbis(2-methyl-4-(4'-tert-butylphenyl)indenyl)titanium dichloride
dimethylsilanediylbis(2-methyl-4-(4'-methylphenyl)indenyl)zirconium dichloride
dimethylsilanediylbis(2-methyl-4-(4'-n-propylphenyl)indenyl)zirconium dichloride
dimethylsilanediylbis(2-methyl-4-(4'-n-butylphenyl)indenyl)zirconium dichloride
dimethylsilanediylbis(2-methyl-4-(4'-hexylphenyl)indenyl)zirconium dichloride
dimethylsilanediylbis(2-methyl-4-(4'-sec-butylphenyl)indenyl)zirconium dichloride
dimethylsilanediylbis(2-ethyl-4-phenyl)indenyl)zirconium dichloride
dimethylsilanediylbis(2-ethyl-4-(4'-methylphenyl)indenyl)zirconium dichloride
dimethylsilanediylbis(2-ethyl-4-(4'-ethylphenyl)indenyl)zirconium dichloride
dimethylsilanediylbis(2-ethyl-4-(4'-n-propylphenyl)indenyl)zirconium dichloride
dimethylsilanediylbis(2-ethyl-4-(4'-n-butylphenyl)indenyl)zirconium dichloride
dimethylsilanediylbis(2-ethyl-4-(4'-hexylphenyl)indenyl)zirconium dichloride
dimethylsilanediylbis(2-ethyl-4-(4'-pentylphenyl)indenyl)zirconium dichloride
dimethylsilanediylbis(2-ethyl-4-(4'-cyclohexylphenyl)indenyl)zirconium dichloride
dimethylsilanediylbis(2-ethyl-4-(4'-sec-butylphenyl)indenyl)zirconium dichloride
dimethylsilanediylbis(2-ethyl-4-(4'-tert-butylphenyl)indenyl)zirconium dichloride
dimethylsilanediylbis(2-n-propyl-4-phenyl)indenyl)zirconium dichloride
dimethylsilanediylbis(2-n-propyl-4-(4'-methylphenyl)indenyl)zirconium dichloride
dimethylsilanediylbis(2-n-propyl-4-(4'-ethylphenyl)indenyl)zirconium dichloride
dimethylsilanediylbis(2-n-propyl-4-(4'-isopropylphenyl)indenyl)zirconium dichloride
dimethylsilanediylbis(2-n-propyl-4-(4'-n-butylphenyl)indenyl)zirconium dichloride
dimethylsilanediylbis(2-n-propyl-4-(4'-hexylphenyl)indenyl)zirconium dichloride
dimethylsilanediylbis(2-n-propyl-4-(4'-cyclohexylphenyl)indenyl)zirconium dichloride
dimethylsilanediylbis(2-n-propyl-4-(4'-sec-butylphenyl)indenyl)zirconium dichloride
dimethylsilanediylbis(2-n-propyl-4-(4'-tert-butylphenyl)indenyl)zirconium dichloride
dimethylsilanediylbis(2-n-butyl-4-phenyl)indenyl)zirconium dichloride
dimethylsilanediylbis(2-n-butyl-4-(4'-methylphenyl)indenyl)zirconium dichloride
dimethylsilanediylbis(2-n-butyl-4-(4'-ethylphenyl)indenyl)zirconium dichloride
dimethylsilanediylbis(2-n-butyl-4-(4'-n-propylphenyl)indenyl)zirconium dichloride
dimethylsilanediylbis(2-n-butyl-4-(4'-isopropylphenyl)indenyl)zirconium dichloride
dimethylsilanediylbis(2-n-butyl-4-(4'-n-butylphenyl)indenyl)zirconium dichloride
dimethylsilanediylbis(2-n-butyl-4-(4'-hexylphenyl)indenyl)zirconium dichloride
dimethylsilanediylbis(2-n-butyl-4-(4'-cyclohexylphenyl)indenyl)zirconium dichloride
dimethylsilanediylbis(2-n-butyl-4-(4'-sec-butylphenyl)indenyl)zirconium dichloride
dimethylsilanediylbis(2-n-butyl-4-(4'-tert-butylphenyl)indenyl)zirconium dichloride dimethylsilanediylbis(2-hexyl-4-phenyl)indenyl)zirconium dichloride
dimethylsilanediylbis(2-hexyl-4-(4'-methylphenyl)indenyl) zirconium dichloride
dimethylsilanediylbis(2-hexyl-4-(4'-ethylphenyl)indenyl) zirconium dichloride
dimethylsilanediylbis(2-hexyl-4-(4'-n-propylphenyl)indenyl)zirconium dichloride
dimethylsilanediylbis(2-hexyl-4-(4'-isopropylphenyl)indenyl)zirconium dichloride
dimethylsilanediylbis(2-hexyl-4-(4'-n-butylphenyl)indenyl) zirconium dichloride
dimethylsilanediylbis(2-hexyl-4-(4'-hexylphenyl)indenyl) zirconium dichloride
dimethylsilanediylbis(2-hexyl-4-(4'-cyclohexylphenyl)indenyl)zirconium dichloride
dimethylsilanediylbis(2-hexyl-4-(4'-sec-butylphenyl)indenyl)zirconium dichloride
dimethylsilanediylbis(2-hexyl-4-(4'-tert-butylphenyl)indenyl)zirconium dichloride
dimethylsilanediylbis(2-methyl-4-(4'-tert-butylphenyl)indenyl) bis(dimethylamide)
dimethylsilanediylbis(2-ethyl-4-(4'-tert-butylphenyl)indenyl)dibenzylzirconium
dimethylsilanediylbis(2-methyl-4-(4'-tert-butylphenyl)indenyl)dimethylzirconium
dimethylgermanediylbis(2-ethyl-4-(4'-tert-butylphenyl)indenyl)zirconium dichloride
dimethylgermanediylbis(2-ethyl-4-(4'-tert-butylphenyl)indenyl)hafnium dichloride
dimethylgermanediylbis(2-propyl-4-(4'-tert-butylphenyl)indenyl)titanium dichloride
dimethylgermanediylbis(2-methyl-4-(4'-tert-butylphenyl) indenyl)zirconium dichloride
ethylidenebis(2-ethyl-4-phenyl)indenyl)zirconium dichloride ethylidenebis(2-ethyl-4-(4'-tert-butylphenyl)indenyl) zirconium dichloride
ethylidenebis(2-n-propyl-4-(4'-tert-butylphenyl)indenyl)zirconium dichloride
ethylidenebis(2-n-butyl-4-(4'-tert-butylphenyl)indenyl)titanium dichloride
ethylidenebis(2-hexyl-4-(4'-tert-butylphenyl)indenyl)dibenzylzirconium
ethylidenebis(2-ethyl-4-(4'-tert-butylphenyl)indenyl)dibenzylhafnium
ethylidenebis(2-methyl-4-(4'-tert-butylphenyl)indenyl) dibenzyltitanium
ethylidenebis(2-methyl-4-(4'-tert-butylphenyl)indenyl)zirconium dichloride
ethylidenebis(2-ethyl-4-(4'-tert-butylphenyl)indenyl)dimethyl hafnium
ethylidenebis(2-n-propyl-4-α-phenyl)indenyl)dimethyltitanium
ethylidenebis(2-ethyl-4-(4'-tert-butylphenyl)indenyl)zirconium bis(dimethylamide)
ethylidenebis(2-ethyl-4-(4'-tert-butylphenyl)indenyl) hafnium bis(dimethylamide)
ethylidenebis(2-ethyl-4-(4'-tert-butylphenyl)indenyl)titanium bis(dimethylamide)
methylethylidenebis(2-ethyl-4-(4'-tert-butylphenyl)indenyl) zirconium dichloride
methylethylidenebis(2-ethyl-4-(4'-tert-butylphenyl)indenyl) hafniumdichloride
phenylphosphinediyl(2-ethyl-4-(4'-tert-butylphenyl)indenyl)zirconium dichloride
phenylphosphinediyl(2-methyl-4-(4'-tert-butylphenyl)indenyl)zirconium dichloride
phenylphosphinediyl(2-ethyl-4-(4'-tert-butylphenyl)indenyl)zirconium dichloride
dimethylsilanediyl(2-methyl-4-azapentalene)(2-methyl-4-(4'-methylphenylindenyl)zirconium dichloride
dimethylsilanediyl(2-methyl-5-azapentalene)(2-methyl-4-(4'-methylphenylindenyl)zirconium dichloride
dimethylsilanediyl(2-methyl-6-azapentalene)(2-methyl-4-(4'-methylphenylindenyl)zirconium dichloride
dimethylsilanediyl(2-methyl-N-phenyl-4-azapentalene)(2-methyl-4-(4'-methylphenylindenyl)zirconium dichloride
dimethylsilanediyl(2-methyl-N-phenyl-5-azapentalene)(2-methyl-4-(4'-methylphenylindenyl)zirconium dichloride
dimethylsilanediyl(2-methyl-N-phenyl-6-azapentalene)(2-methyl-4-(4'-methylphenylindenyl)zirconium dichloride
dimethylsilanediyl(2,5-dimethyl-4-azapentalene)(2-methyl-4-(4'-methylphenylindenyl)zirconium dichloride
dimethylsilanediyl(2,5-dimethyl-6-azapentalene)(2-methyl-4-(4'-methylphenylindenyl)zirconium dichloride
dimethylsilanediyl(2,5-dimethyl-N-phenyl-4-azapentalene) (2-methyl-4-(4'-methylphenylindenyl)zirconium dichloride
dimethylsilanediyl(2,5-dimethyl-N-phenyl-6-azapentalene) (2-methyl-4-(4'-methylphenylindenyl)zirconium dichloride
dimethylsilanediyl(2-methyl-4-thiapentalene)(2-methyl-4-(4'-methylphenylindenyl)zirconium dichloride
dimethylsilanediyl(2-methyl-5-thiapentalene)(2-methyl-4-(4'-methylphenylindenyl)zirconium dichloride
dimethylsilanediyl(2-methyl-6-thiapentalene)($^2$-methyl-4-(4'-methylphenylindenyl)zirconium dichloride
dimethylsilanediyl(2,5-dimethyl-4-thiapentalene)(2-methyl-4-(4'-methylphenylindenyl)zirconium dichloride
dimethylsilanediyl(2,5-dimethyl-6-thiapentalene)(2-methyl-4-(4'-methylphenylindenyl)zirconium dichloride
dimethylsilanediyl(2-methyl-4-oxapentalene)(2-methyl-4-(4'-methylphenylindenyl)zirconium dichloride
dimethylsilanediyl(2-methyl-5-oxapentalene)(2-methyl-4-(4'-methylphenylindenyl)zirconium dichloride
dimethylsilanediyl(2-methyl-6-oxapentalene)(2-methyl-4-(4'-5 methylphenylindenyl)zirconium dichloride
dimethylsilanediyl(2,5-dimethyl-4-oxapentalene)(2-methyl-4-(4'-methylphenylindenyl)zirconium dichloride
dimethylsilanediyl(2,5-dimethyl-6-oxapentalene)(2-methyl-4-(4'-methylphenylindenyl)zirconium dichloride
dimethylsilanediyl(2-methyl-4-azapentalene)(2-methyl-4-(4'-ethylphenylindenyl)zirconium dichloride
dimethylsilanediyl(2-methyl-5-azapentalene)(2-methyl-4-(4'-ethylphenylindenyl)zirconium dichloride
dimethylsilanediyl(2-methyl-6-azapentalene)(2-methyl-4-(4'-ethylphenylindenyl)zirconium dichloride
dimethylsilanediyl(2-methyl-N-phenyl-4-azapentalene)(2-methyl-4-(4'-ethylphenylindenyl)zirconium dichloride
dimethylsilanediyl(2-methyl-N-phenyl-5-azapentalene)(2-methyl-4-(4'-ethylphenylindenyl)zirconium dichloride
dimethylsilanediyl(2-methyl-N-phenyl-6-azapentalene)(2-methyl-4-(4'-ethylphenylindenyl)zirconium dichloride
dimethylsilanediyl(2,5-dimethyl-4-azapentalene)(2-methyl-4-(4'-ethylphenylindenyl)zirconium dichloride
dimethylsilanediyl(2,5-dimethyl-6-azapentalene)(2-methyl-4-(4'-ethylphenylindenyl)zirconium dichloride
dimethylsilanediyl(2,5-dimethyl-N-phenyl-4-azapentalene) (2-methyl-4-(4'-ethylphenylindenyl)zirconium dichloride
dimethylsilanediyl(2,5-dimethyl-N-phenyl-6-azapentalene) (2-methyl-4-(4'-ethylphenylindenyl)zirconium dichloride
dimethylsilanediyl(2-methyl-4-thiapentalene)(2-methyl-4-(4'-ethylphenylindenyl)zirconium dichloride dimethylsilanediyl(2-methyl-5-thiapentalene)(2-methyl-4-(4'-ethylphenylindenyl)zirconium dichloride
dimethylsilanediyl(2-methyl-6-thiapentalene)(2-methyl-4-(4'-ethylphenylindenyl)zirconium dichloride
dimethylsilanediyl(2,5-dimethyl-4-thiapentalene)(2-methyl-4-(4'-ethylphenylindenyl)zirconium dichloride
dimethylsilanediyl(2,5-dimethyl-6-thiapentalene)(2-methyl-4-(4'-ethylphenylindenyl)zirconium dichloride
dimethylsilanediyl(2-methyl-4-oxapentalene)(2-methyl-4-(4'-ethylphenylindenyl)zirconium dichloride
dimethylsilanediyl(2-methyl-5-oxapentalene)(2-methyl-4-(4'-ethylphenylindenyl)zirconium dichloride
dimethylsilanediyl(2-methyl-6-oxapentalene)(2-methyl-4-(4'-ethylphenylindenyl)zirconium dichloride
dimethylsilanediyl(2,5-dimethyl-4-oxapentalene)(2-methyl-4-(4'-ethylphenylindenyl)zirconium dichloride
dimethylsilanediyl(2,5-dimethyl-6-oxapentalene)(2-methyl-4-(4'-ethylphenylindenyl)zirconium dichloride
dimethylsilanediyl(2-methyl-4-azapentalene)(2-methyl-4-(4'-n-propylphenylindenyl)zirconium dichloride
dimethylsilanediyl(2-methyl-5-azapentalene)(2-methyl-4-(4'-n-propylphenylindenyl)zirconium dichloride
dimethylsilanediyl(2-methyl-6-azapentalene)(2-methyl-4-(4'-n-propylphenylindenyl)zirconium dichloride
dimethylsilanediyl(2-methyl-N-phenyl-4-azapentalene)(2-methyl-4-(4'-n-propylphenylindenyl)zirconium dichloride
dimethylsilanediyl(2-methyl-N-phenyl-5-azapentalene)(2-methyl-4-(4'-n-propylphenylindenyl)zirconium dichloride
dimethylsilanediyl(2-methyl-N-phenyl-6-azapentalene)(2-methyl-4-(4'-n-propylphenylindenyl)zirconium dichloride
dimethylsilanediyl(2,5-dimethyl-4-azapentalene)(2-methyl-4-(4'-n-propylphenylindenyl)zirconium dichloride
dimethylsilanediyl(2,5-dimethyl-6-azapentalene)(2-methyl-4-(4'-n-propylphenylindenyl)zirconium dichloride
dimethylsilanediyl(2,5-dimethyl-N-phenyl-4-azapentalene)(2-methyl-4-(4'-n-propylphenylindenyl)zirconium dichloride
dimethylsilanediyl(2,5-dimethyl-N-phenyl-6-azapentalene)(2-methyl-4-(4'-n-propylphenylindenyl)zirconium dichloride
dimethylsilanediyl(2-methyl-4-thiapentalene)(2-methyl-4-(4'-n-propylphenylindenyl)zirconium dichloride
dimethylsilanediyl(2-methyl-5-thiapentalene)(2-methyl-4-(4'-n-propylphenylindenyl)zirconium dichloride
dimethylsilanediyl(2-methyl-6-thiapentalene)(2-methyl-4-(4'-n-propylphenylindenyl)zirconium dichloride
dimethylsilanediyl(2,5-dimethyl-4-thiapentalene)(2-methyl-4-(4'-n-propylphenylindenyl)zirconium dichloride
dimethylsilanediyl(2,5-dimethyl-6-thiapentalene)(2-methyl-4-(4'-n-propylphenylindenyl)zirconium dichloride
dimethylsilanediyl(2-methyl-4-oxapentalene)(2-methyl-4-(4'-n-propylphenylindenyl)zirconium dichloride
dimethylsilanediyl(2-methyl-5-oxapentalene)(2-methyl-4-(4'-n-propylphenylindenyl)zirconium dichloride
dimethylsilanediyl(2-methyl-6-oxapentalene)(2-methyl-4-(4'-n-propylphenylindenyl)zirconium dichloride
dimethylsilanediyl(2,5-dimethyl-4-oxapentalene)(2-methyl-4-(4'-n-propylphenylindenyl)zirconium dichloride
dimethylsilanediyl(2,5-dimethyl-6-oxapentalene)(2-methyl-4-(4'-n-propylphenylindenyl)zirconium dichloride
dimethylsilanediyl(2-methyl-4-azapentalene)(2-methyl-4-(4'-isopropylphenylindenyl)zirconium dichloride
dimethylsilanediyl(2-methyl-5-azapentalene)(2-methyl-4-(4'-isopropylphenylindenyl)zirconium dichloride
dimethylsilanediyl(2-methyl-6-azapentalene)(2-methyl-4-(4'-isopropylphenylindenyl)zirconium dichloride
dimethylsilanediyl(2-methyl-N-phenyl-4-azapentalene)(2-methyl-4-(4'-isopropylphenylindenyl)zirconium dichloride
dimethylsilanediyl(2-methyl-N-phenyl-5-azapentalene)(2-methyl-4-(4'-isopropylphenylindenyl)zirconium dichloride
dimethylsilanediyl(2-methyl-N-phenyl-6-azapentalene)(2-methyl-4-(4'-isopropylphenylindenyl)zirconium dichloride
dimethylsilanediyl(2,5-dimethyl-4-azapentalene)(2-methyl-4-(4'-isopropylphenylindenyl)zirconium dichloride
dimethylsilanediyl(2,5-dimethyl-6-azapentalene)(2-methyl-4-(4'-isopropylphenylindenyl)zirconium dichloride
dimethylsilanediyl(2,5-dimethyl-N-phenyl-4-azapentalene)(2-methyl-4-(4'-isopropylphenylindenyl)zirconium dichloride
dimethylsilanediyl(2,5-dimethyl-N-phenyl-6-azapentalene)(2-methyl-4-(4'-isopropylphenylindenyl)zirconium dichloride
dimethylsilanediyl(2-methyl-4-thiapentalene)(2-methyl-4-(4'-isopropylphenylindenyl)zirconium dichloride
dimethylsilanediyl(2-methyl-5-thiapentalene)(2-methyl-4-(4'-isopropylphenylindenyl)zirconium dichloride
dimethylsilanediyl(2-methyl-6-thiapentalene)(2-methyl-4-(4'-isopropylphenylindenyl)zirconium dichloride
dimethylsilanediyl(2,5-dimethyl-4-thiapentalene)(2-methyl-4-(4'-isopropylphenylindenyl)zirconium dichloride
dimethylsilanediyl(2,5-dimethyl-6-thiapentalene)(2-methyl-4-(4'-isopropylphenylindenyl)zirconium dichloride
dimethylsilanediyl(2-methyl-4-oxapentalene)(2-methyl-4-(4'-isopropylphenylindenyl)zirconium dichloride
dimethylsilanediyl(2-methyl-5-oxapentalene)(2-methyl-4-(4'-isopropylphenylindenyl)zirconium dichloride
dimethylsilanediyl(2-methyl-6-oxapentalene)(2-methyl-4-(4'-isopropylphenylindenyl)zirconium dichloride
dimethylsilanediyl(2,5-dimethyl-4-oxapentalene)(2-methyl-4-(4'isopropylphenylindenyl)zirconium dichloride
dimethylsilanediyl(2,5-dimethyl-6-oxapentalene)(2-methyl-4-(4'-isopropylphenylindenyl)zirconium dichloride
dimethylsilanediyl(2-methyl-4-azapentalene)(2-methyl-4-(4'-n-butylphenylindenyl)zirconium dichloride
dimethylsilanediyl(2-methyl-5-azapentalene)(2-methyl-4-(4'-n-butylphenylindenyl)zirconium dichloride
dimethylsilanediyl(2-methyl-6-azapentalene)(2-methyl-4-(4'-n-butylphenylindenyl)zirconium dichloride
dimethylsilanediyl(2-methyl-N-phenyl-4-azapentalene)(2-methyl-4-(4'-n-butylphenylindenyl)zirconium dichloride
dimethylsilanediyl(2-methyl-N-phenyl-5-azapentalene)(2-methyl-4-(4'-n-butylphenylindenyl)zirconium dichloride
dimethylsilanediyl(2-methyl-N-phenyl-6-azapentalene)(2-methyl-4-(4'-n-butylphenylindenyl)zirconium dichloride
dimethylsilanediyl(2,5-dimethyl-4-azapentalene)(2-methyl-4-(4'-n-butylphenylindenyl)zirconium dichloride
dimethylsilanediyl(2,5-dimethyl-6-azapentalene)(2-methyl-4-(4'-n-butylphenylindenyl)zirconium dichloride
dimethylsilanediyl(2,5-dimethyl-N-phenyl-4-azapentalene)(2-methyl-4-(4'-n-butylphenylindenyl)zirconium dichloride
dimethylsilanediyl(2,5-dimethyl-N-phenyl-6-azapentalene)(2-methyl-4-(4'-n-butylphenylindenyl)zirconium dichloride
dimethylsilanediyl(2-methyl-4-thiapentalene)(2-methyl-4-(4'-n-butylphenylindenyl)zirconium dichloride
dimethylsilanediyl(2-methyl-5-thiapentalene)(2-methyl-4-(4'-n-butylphenylindenyl)zirconium dichloride dimethylsilanediyl(2-methyl-6-thiapentalene)(2-methyl-4-(4'-n-butylphenylindenyl)zirconium dichloride
dimethylsilanediyl(2,5-dimethyl-4-thiapentalene)(2-methyl-4-(4'-n-butylphenylindenyl)zirconium dichloride
dimethylsilanediyl(2,5-dimethyl-6-thiapentalene)(2-methyl-4-(4'-n-butylphenylindenyl)zirconium dichloride
dimethylsilanediyl(2-methyl-4-oxapentalene)(2-methyl-4-(4'-n-butylphenylindenyl)zirconium dichloride
dimethylsilanediyl(2-methyl-5-oxapentalene)(2-methyl-4-(4'-n-butylphenylindenyl)zirconium dichloride
dimethylsilanediyl(2-methyl-6-oxapentalene)(2-methyl-4-(4'-n-butylphenylindenyl)zirconium dichloride
dimethylsilanediyl(2,5-dimethyl-4-oxapentalene)(2-methyl-4-(4'-n-butylphenylindenyl)zirconium dichloride
dimethylsilanediyl(2,5-dimethyl-6-oxapentalene)(2-methyl-4-(4'-n-butylphenylindenyl)zirconium dichloride
dimethylsilanediyl(2-methyl-4-azapentalene)(2-methyl-4-(4'-s-butylphenylindenyl)zirconium dichloride
dimethylsilanediyl(2-methyl-5-azapentalene)(2-methyl-4-(4'-s-butylphenylindenyl)zirconium dichloride
dimethylsilanediyl(2-methyl-6-azapentalene)(2-methyl-4-(4'-s-butylphenylindenyl)zirconium dichloride
dimethylsilanediyl(2-methyl-N-phenyl-4-azapentalene)(2-methyl-4-(4'-s-butylphenylindenyl)zirconium dichloride
dimethylsilanediyl(2-methyl-N-phenyl-5-azapentalene)(2-methyl-4-(4'-s-butylphenylindenyl)zirconium dichloride
dimethylsilanediyl(2-methyl-N-phenyl-6-azapentalene)(2-methyl-4-(4'-s-butylphenylindenyl)zirconium dichloride
dimethylsilanediyl(2,5-dimethyl-4-azapentalene)(2-methyl-4-(4'-s-butylphenylindenyl)zirconium dichloride
dimethylsilanediyl(2,5-dimethyl-6-azapentalene)(2-methyl-4-(4'-s-butylphenylindenyl)zirconium dichloride
dimethylsilanediyl(2,5-dimethyl-N-phenyl-4-azapentalene)(2-ethyl-4-(4'-s-butylphenylindenyl)zirconium dichloride
dimethylsilanediyl(2,5-dimethyl-N-phenyl-6-azapentalene)(2-ethyl-4-(4'-s-butylphenylindenyl)zirconium dichloride
dimethylsilanediyl(2-methyl-4-thiapentalene)(2-methyl-4-(4'-s-butylhenylindenyl)zirconium dichloride
dimethylsilanediyl(2-methyl-5-thiapentalene)(2-methyl-4-(4'-s-butylphenylindenyl)zirconium dichloride
dimethylsilanediyl(2-methyl-6-thiapentalene)(2-methyl-4-(4'-s-butylphenylindenyl)zirconium dichloride
dimethylsilanediyl(2,5-dimethyl-4-thiapentalene)(2-methyl-4-(4'-s-butylphenylindenyl)zirconium dichloride
dimethylsilanediyl(2,5-dimethyl-6-thiapentalene)(2-methyl-4-(4'-s-butylphenylindenyl)zirconium dichloride
dimethylsilanediyl(2-methyl-4-oxapentalene)(2-methyl-4-(4'-s-butylphenylindenyl)zirconium dichloride
dimethylsilanediyl(2-methyl-5-oxapentalene)(2-methyl-4-(4'-s-butylphenylindenyl)zirconium dichloride
dimethylsilanediyl(2-methyl-6-oxapentalene)(2-methyl-4-(4'-s-butylphenylindenyl)zirconium dichloride
dimethylsilanediyl(2,5-dimethyl-4-oxapentalene)(2-methyl-4-(4'-s-butylphenylindenyl)zirconium dichloride
dimethylsilanediyl(2,5-dimethyl-6-oxapentalene)(2-methyl-4-(4'-s-butylphenylindenyl)zirconium dichloride
dimethylsilanediyl(2-methyl-4-azapentalene)(2-methyl-4-(4'-tert-butylphenylindenyl)zirconium dichloride
dimethylsilanediyl(2-methyl-5-azapentalene)(2-methyl-4-(4'-tert-butylphenylindenyl)zirconium dichloride
dimethylsilanediyl(2-methyl-6-azapentalene)(2-methyl-4-(4'-tert-butylphenylindenyl)zirconium dichloride
dimethylsilanediyl(2-methyl-N-phenyl-4-azapentalene)(2-methyl-4-(4'-tert-butylphenylindenyl)zirconium dichloride
dimethylsilanediyl(2-methyl-N-phenyl-5-azapentalene)(2-methyl-4-(4'-tert-butylphenylindenyl)zirconium dichloride
dimethylsilanediyl(2-methyl-N-phenyl-6-azapentalene)(2-methyl-4-(4'-tert-butylphenylindenyl)zirconium dichloride
dimethylsilanediyl(2,5-dimethyl-4-azapentalene)(2-methyl-4-(4'-tert-butylphenylindenyl)zirconium dichloride
dimethylsilanediyl(2,5-dimethyl-6-azapentalene)(2-methyl-4-(4'-tert-butylphenylindenyl)zirconium dichloride
dimethylsilanediyl(2,5-dimethyl-N-phenyl-4-azapentalene)(2-methyl-4-(4'-tert-butylphenylindenyl)zirconium dichloride
dimethylsilanediyl(2,5-dimethyl-N-phenyl-6-azapentalene)(2-methyl-4-(4'-tert-butylphenylindenyl)zirconium dichloride
dimethylsilanediyl(2-methyl-4-thiapentalene)(2-methyl-4-(4'-tert-butylphenylindenyl)zirconium dichloride
dimethylsilanediyl(2-methyl-5-thiapentalene)(2-methyl-4-(4'-tert-butylphenylindenyl)zirconium dichloride
dimethylsilanediyl(2-methyl-6-thiapentalene)(2-methyl-4-(4'-tert-butylphenylindenyl)zirconium dichloride
dimethylsilanediyl(2,5-dimethyl-4-thiapentalene)(2-methyl-4-(4'-tert-butylphenylindenyl)zirconium dichloride
dimethylsilanediyl(2,5-dimethyl-6-thiapentalene)(2-methyl-4-(4'-tert-butylphenylindenyl)zirconium dichloride
dimethylsilanediyl(2-methyl-4-oxapentalene)(2-methyl-4-(4'-tert-butylphenylindenyl)zirconium dichloride
dimethylsilanediyl(2-methyl-5-oxapentalene)(2-methyl-4-(4'-tert-butylphenylindenyl)zirconium dichloride
dimethylsilanediyl(2-methyl-6-oxapentalene)(2-methyl-4-(4'-tert-butylphenylindenyl)zirconium dichloride
dimethylsilanediyl(2,5-dimethyl-4-oxapentalene)(2-methyl-4-(4'-tert-butylphenylindenyl)zirconium dichloride
dimethylsilanediyl(2,5-dimethyl-6-oxapentalene)(2-methyl-4-(4'-tert-butylphenylindenyl)zirconium dichloride
dimethylsilanediyl(2-methyl-4-azapentalene)(2-methyl-4-(4'-n-pentylphenylindenyl)zirconium dichloride
dimethylsilanediyl(2-methyl-5-azapentalene)(2-methyl-4-(4'-n-pentylphenylindenyl)zirconium dichloride
dimethylsilanediyl(2-methyl-6-azapentalene)(2-methyl-4-(4'-n-pentylphenylindenyl)zirconium dichloride
dimethylsilanediyl(2-methyl-N-phenyl-4-azapentalene)(2-methyl-4-(4'-n-pentylphenylindenyl)zirconium dichloride
dimethylsilanediyl(2-methyl-N-phenyl-5-azapentalene)(2-methyl-4-(4'-n-pentylphenylindenyl)zirconium dichloride
dimethylsilanediyl(2-methyl-N-phenyl-6-azapentalene)(2-methyl-4-(4'-n-pentylphenylindenyl)zirconium dichloride
dimethylsilanediyl(2,5-dimethyl-4-azapentalene)(2-methyl-4-(4'-n-pentylphenylindenyl)zirconium dichloride
dimethylsilanediyl(2,5-dimethyl-6-azapentalene)(2-methyl-4-(4'-n-pentylphenylindenyl)zirconium dichloride
dimethylsilanediyl(2,5-dimethyl-N-phenyl-4-azapentalene)(2-methyl-4-(4'-n-pentylphenylindenyl)zirconium dichloride
dimethylsilanediyl(2,5-dimethyl-N-phenyl-6-azapentalene)(2-methyl-4-(4'-n-pentylphenylindenyl)zirconium dichloride
dimethylsilanediyl(2-methyl-4-thiapentalene)(2-methyl-4-(4'-n-pentylphenylindenyl)zirconium dichloride
dimethylsilanediyl(2-methyl-5-thiapentalene)(2-methyl-4-(4'-n-pentylphenylindenyl)zirconium dichloride
dimethylsilanediyl(2-methyl-6-thiapentalene)(2-methyl-4-(4'-n-pentylphenylindenyl)zirconium dichloride
dimethylsilanediyl(2,5-dimethyl-4-thiapentalene)(2-methyl-4-(4'-n-pentylphenylindenyl)zirconium dichloride dimethylsilanediyl(2,5-dimethyl-6-thiapentalene)(2-methyl-4-(4'-n-pentylphenylindenyl)zirconium dichloride
dimethylsilanediyl(2-methyl-4-oxapentalene)(2-methyl-4-(4'-n-pentylphenylindenyl)zirconium dichloride
dimethylsilanediyl(2-methyl-5-oxapentalene)(2-methyl-4-(4'-n-pentylphenylindenyl)zirconium dichloride
dimethylsilanediyl(2-methyl-6-oxapentalene)(2-methyl-4-(4'-n-pentylphenylindenyl)zirconium dichloride
dimethylsilanediyl(2,5-dimethyl-4-oxapentalene)(2-methyl-4-(4'-n-pentylphenylindenyl)zirconium dichloride
dimethylsilanediyl(2,5-dimethyl-6-oxapentalene)(2-methyl-4-(4'-n-pentylphenylindenyl)zirconium dichloride
dimethylsilanediyl(2-methyl-4-azapentalene)(2-methyl-4-(4'-n-hexylphenylindenyl)zirconium dichloride
dimethylsilanediyl(2-methyl-5-azapentalene)(2-methyl-4-(4'-n-hexylphenylindenyl)zirconium dichloride
dimethylsilanediyl(2-methyl-6-azapentalene)(2-methyl-4-(4'-n-hexylphenylindenyl)zirconium dichloride
dimethylsilanediyl(2-methyl-N-phenyl-4-azapentalene)(2-methyl-4-(4'-n-hexylphenylindenyl)zirconium dichloride
dimethylsilanediyl(2-methyl-N-phenyl-5-azapentalene)(2-methyl-4-(4'-n-hexylphenylindenyl)zirconium dichloride
dimethylsilanediyl(2-methyl-N-phenyl-6-azapentalene)(2-methyl-4-(4'-n-hexylphenylindenyl)zirconium dichloride
dimethylsilanediyl(2,5-dimethyl-4-azapentalene)(2-methyl-4-(4-n-hexylphenylindenyl)zirconium dichloride
dimethylsilanediyl(2,5-dimethyl-6-azapentalene)(2-methyl-4-(4'-n-hexylphenylindenyl)zirconium dichloride
dimethylsilanediyl(2,5-dimethyl-N-phenyl-4-azapentalene)(2-methyl-4-(4'-n-hexylphenylindenyl)zirconium dichloride
dimethylsilanediyl(2,5-dimethyl-N-phenyl-6-azapentalene)(2-methyl-4-(4'-n-hexylphenylindenyl)zirconium dichloride
dimethylsilanediyl(2-methyl-4-thiapentalene)(2-methyl-4-(4'-n-hexylphenylindenyl)zirconium dichloride
dimethylsilanediyl(2-methyl-5-thiapentalene)(2-methyl-4-(4'-n-hexylphenylindenyl)zirconium dichloride
dimethylsilanediyl(2-methyl-6-thiapentalene)(2-methyl-4-(4'-n-hexylphenylindenyl)zirconium dichloride
dimethylsilanediyl(2,5-dimethyl-4-thiapentalene)(2-methyl-4-(4'-n-hexylphenylindenyl)zirconium dichloride
dimethylsilanediyl(2,5-dimethyl-6-thiapentalene)(2-methyl-4-(4'-n-hexylphenylindenyl)zirconium dichloride
dimethylsilanediyl(2-methyl-4-oxapentalene)(2-methyl-4-(4'-n-hexylphenylindenyl)zirconium dichloride
dimethylsilanediyl(2-methyl-5-oxapentalene)(2-methyl-4-(4'-n-hexylphenylindenyl)zirconium dichloride
dimethylsilanediyl(2-methyl-6-oxapentalene)(2-methyl-4-(4'-n-hexylphenylindenyl)zirconium dichloride
dimethylsilanediyl(2,5-dimethyl-4-oxapentalene)(2-methyl-4-(4'-n-hexylphenylindenyl)zirconium dichloride
dimethylsilanediyl(2,5-dimethyl-6-oxapentalene)(2-methyl-4-(4'-n-hexylphenylindenyl)zirconium dichloride
dimethylsilanediyl(2-methyl-4-azapentalene)(2-methyl-4-(4'-cyclohexylphenylindenyl)zirconium dichloride
dimethylsilanediyl(2-methyl-5-azapentalene)(2-methyl-4-(4'-cyclohexylphenylindenyl)zirconium dichloride
dimethylsilanediyl(2-methyl-6-azapentalene)(2-methyl-4-(4'-cyclohexylphenylindenyl)zirconium dichloride
dimethylsilanediyl(2-methyl-N-phenyl-4-azapentalene)(2-methyl-4-(4'-cyclohexylphenylindenyl)zirconium dichloride
dimethylsilanediyl(2-methyl-N-phenyl-5-azapentalene)(2-methyl-4-(4'-cyclohexylphenylindenyl)zirconium dichloride
dimethylsilanediyl(2-methyl-N-phenyl-6-azapentalene)(2-methyl-4-(4'-cyclohexylphenylindenyl)zirconium dichloride
dimethylsilanediyl(2,5-dimethyl-4-azapentalene)(2-methyl-4-(4'-cyclohexylphenylindenyl)zirconium dichloride
dimethylsilanediyl(2,5-dimethyl-6-azapentalene)(2-methyl-4-(4'-cyclohexylphenylindenyl)zirconium dichloride
dimethylsilanediyl(2,5-dimethyl-N-phenyl-4-azapentalene)(2-methyl-4-(4'-cyclohexylphenylindenyl)zirconium dichloride
dimethylsilanediyl(2,5-dimethyl-N-phenyl-6-azapentalene)(2-methyl-4-(4'-cyclohexylphenylindenyl)zirconium dichloride
dimethylsilanediyl(2-methyl-4-thiapentalene)(2-methyl-4-(4'-cyclohexylphenylindenyl)zirconium dichloride
dimethylsilanediyl(2-methyl-5-thiapentalene)(2-methyl-4-(4'-cyclohexylphenylindenyl)zirconium dichloride
dimethylsilanediyl(2-methyl-6-thiapentalene)(2-methyl-4-(4'-cyclohexylphenylindenyl)zirconium dichloride
dimethylsilanediyl(2,5-dimethyl-4-thiapentalene)(2-methyl-4-(4'-cyclohexylphenylindenyl)zirconium dichloride
dimethylsilanediyl(2,5-dimethyl-6-thiapentalene)(2-methyl-4-(4'-cyclohexylphenylindenyl)zirconium dichloride
dimethylsilanediyl(2-methyl-4-oxapentalene)(2-methyl-4-(4'-cyclohexylphenylindenyl)zirconium dichloride
dimethylsilanediyl(2-methyl-5-oxapentalene)(2-methyl-4-(4'-cyclohexylphenylindenyl)zirconium dichloride
dimethylsilanediyl(2-methyl-6-oxapentalene)(2-methyl-4-(4'-cyclohexylphenylindenyl)zirconium dichloride
dimethylsilanediyl(2,5-dimethyl-4-oxapentalene)(2-methyl-4-(4'-cyclohexylphenylindenyl)zirconium dichloride
dimethylsilanediyl(2,5-dimethyl-6-oxapentalene)(2-methyl-4-(4'-cyclohexylphenylindenyl)zirconium dichloride
dimethylsilanediyl(2-methyl-4-azapentalene)(2-methyl-4-(4'-trimethylsilylphenylindenyl)zirconium dichloride
dimethylsilanediyl(2-methyl-5-azapentalene)(2-methyl-4-(4'-trimethylsilylphenylindenyl)zirconium dichloride
dimethylsilanediyl(2-methyl-6-azapentalene)(2-methyl-4-(4'-trimethylsilylphenylindenyl)zirconium dichloride
dimethylsilanediyl(2-methyl-N-phenyl-4-azapentalene)(2-methyl-4-(4'-trimethylsilylphenylindenyl)zirconium dichloride
dimethylsilanediyl(2-methyl-N-phenyl-5-azapentalene)(2-methyl-4-(4'-trimethylsilylphenylindenyl)zirconium dichloride
dimethylsilanediyl(2-methyl-N-phenyl-6-azapentalene)(2-methyl-4-(4'-trimethylsilylphenylindenyl)zirconium dichloride
dimethylsilanediyl(2,5-dimethyl-4-azapentalene)(2-methyl-4-(4'-trimethylsilylphenylindenyl)zirconium dichloride
dimethylsilanediyl(2,5-dimethyl-6-azapentalene)(2-methyl-4-(4'-trimethylsilylphenylindenyl)zirconium dichloride
dimethylsilanediyl(2,5-dimethyl-N-phenyl-4-azapentalene)(2-methyl-4-(4'-trimethylsilylphenylindenyl)zirconium dichloride
dimethylsilanediyl(2,5-dimethyl-N-phenyl-6-azapentalene)(2-methyl-4-(4'-trimethylsilylphenylindenyl)zirconium dichloride
dimethylsilanediyl(2-methyl-4-thiapentalene)(2-methyl-4-(4'-trimethylsilylphenylindenyl)zirconium dichloride
dimethylsilanediyl(2-methyl-5-thiapentalene) (2-methyl-4-(4'-trimethylsilylphenylindenyl)zirconium dichloride
dimethylsilanediyl(2-methyl-6-thiapentalene)(2-methyl-4-(4'-5 trimethylsilylphenylindenyl)zirconium dichloride
dimethylsilanediyl(2,5-dimethyl-4-thiapentalene)(2-methyl-4-(4'-trimethylsilylphenylindenyl)zirconium dichloride dimethylsilanediyl(2,5-dimethyl-6-thiapentalene)(2-methyl-4-(4'-trimethylsilylphenylindenyl)zirconium dichloride
dimethylsilanediyl(2-methyl-4-oxapentalene)(2-methyl-4-(4'-trimethylsilylphenylindenyl)zirconium dichloride
dimethylsilanediyl(2-methyl-5-oxapentalene)(2-methyl-4-(4'-trimethylsilylphenylindenyl)zirconium dichloride
dimethylsilanediyl(2-methyl-6-oxapentalene)(2-methyl-4-(4'-trimethylsilylphenylindenyl)zirconium dichloride
dimethylsilanediyl(2,5-dimethyl-4-oxapentalene)(2-methyl-4-(4'-trimethylsilylphenylindenyl)zirconium dichloride
dimethylsilanediyl(2,5-dimethyl-6-oxapentalene)(2-methyl-4-(4'-trimethylsilylphenylindenyl)zirconium dichloride
dimethylsilanediyl(2-methyl-4-azapentalene)(2-methyl-4-(4'-adamantylphenylindenyl)zirconium dichloride
dimethylsilanediyl(2-methyl-5-azapentalene)(2-methyl-4-(4'-adamantylphenylindenyl)zirconium dichloride
dimethylsilanediyl(2-methyl-6-azapentalene)(2-methyl-4-(4'-adamantylphenylindenyl)zirconium dichloride
dimethylsilanediyl(2-methyl-N-phenyl-4-azapentalene)(2-methyl-4-(4'-adamantylphenylindenyl)zirconium dichloride
dimethylsilanediyl(2-methyl-N-phenyl-5-azapentalene)(2-methyl-4-(4'-adamantylphenylindenyl)zirconium dichloride
dimethylsilanediyl(2-methyl-N-phenyl-6-azapentalene)(2-methyl-4-(4'-adamantylphenylindenyl)zirconium dichloride
dimethylsilanediyl(2,5-dimethyl-4-azapentalene)(2-methyl-4-(4'-adamantylphenylindenyl)zirconium dichloride
dimethylsilanediyl(2,5-dimethyl-6-azapentalene)(2-methyl-4-(4'-adamantylphenylindenyl)zirconium dichloride
dimethylsilanediyl(2,5-dimethyl-4-azapentalene)(2-methyl-4-(4'-adamantylphenylindenyl)zirconium dichloride
dimethylsilanediyl(2,5-dimethyl-N-phenyl-4-azapentalene)(2-methyl-4-(4'-adamantylphenylindenyl)zirconium dichloride
dimethylsilanediyl(2,5-dimethyl-N-phenyl-6-azapentalene)(2-methyl-4-(4'-adamantylphenylindenyl)zirconium dichloride
dimethylsilanediyl(2-methyl-4-thiapentalene)(2-methyl-4-(4'-adamantylphenylindenyl)zirconium dichloride
dimethylsilanediyl(2-methyl-5-thiapentalene)(2-methyl-4-(4'-adamantylphenylindenyl)zirconium dichloride
dimethylsilanediyl(2-methyl-6-thiapentalene)(2-methyl-4-(4'-adamantylphenylindenyl)zirconium dichloride
dimethylsilanediyl(2,5-dimethyl-4-thiapentalene)(2-methyl-4-(4'-adamantylphenylindenyl)zirconium dichloride
dimethylsilanediyl(2,5-dimethyl-6-thiapentalene)(2-methyl-4-(4'-adamantylphenylindenyl)zirconium dichloride
dimethylsilanediyl(2-methyl-4-oxapentalene)(2-methyl-4-(4'-adamantylphenylindenyl)zirconium dichloride
dimethylsilanediyl(2-methyl-5-oxapentalene)(2-methyl-4-(4'-adamantylphenylindenyl)zirconium dichloride
dimethylsilanediyl(2-methyl-6-oxapentalene)(2-methyl-4-(4'-adamantylphenylindenyl)zirconium dichloride
dimethylsilanediyl(2,5-dimethyl-4-oxapentalene)(2-methyl-4-(4'-adamantylphenylindenyl)zirconium dichloride
dimethylsilanediyl(2,5-dimethyl-6-oxapentalene)(2-methyl-4-(4'-adamantylphenylindenyl)zirconium dichloride
dimethylsilanediyl(2-methyl-4-azapentalene)(2-methyl-4-(4'-tris(trifluoromethyl)methylphenylindenyl)zirconium dichloride
dimethylsilanediyl(2-methyl-5-azapentalene)(2-methyl-4-(4'-tris(trifluoromethyl)methylphenylindenyl)zirconium dichloride
dimethylsilanediyl(2-methyl-6-azapentalene)(2-methyl-4-(4'-tris(trifluoromethyl)methylphenylindenyl)zirconium dichloride
dimethylsilanediyl(2-methyl-N-phenyl-4-azapentalene)(2-methyl-4-(4'-tris(trifluoromethyl)methylphenylindenyl)zirconium dichloride
dimethylsilanediyl(2-methyl-N-phenyl-5-azapentalene)(2-methyl-4-(4'-tris(trifluoromethyl)methylphenylindenyl)zirconium dichloride
dimethylsilanediyl(2-methyl-N-phenyl-6-azapentalene)(2-methyl-4-(4'-tris(trifluoromethyl)methylphenylindenyl)zirconium dichloride
dimethylsilanediyl(2,5-dimethyl-4-azapentalene)(2-methyl-4-(4'-trifluorbmethyl)methylphenylindenyl)zirconium dichloride
dimethylsilanediyl(2,5-dimethyl-6-azapentalene)(2-methyl-4-(4'-tris(trifluoromethyl)methylphenylindenyl)zirconium dichloride
dimethylsilanediyl(2,5-dimethyl-N-phenyl-4-azapentalene)(2-methyl-4-(4'-tris(trifluoromethyl)methylphenylindenyl)zirconium dichloride
dimethylsilanediyl(2,5-dimethyl-N-phenyl-6-azapentalene)(2-methyl-4-(4'-tris(trifluoromethyl)methylphenylindenyl)zirconium dichloride
dimethylsilanediyl(2-methyl-4-thiapentalene)(2-methyl-4-(4'-tris(trifluoromethyl)methylphenylindenyl)zirconium dichloride
dimethylsilanediyl(2-methyl-5-thiapentalene)(2-methyl-4-(4'-tris(trifluoromethyl)methylphenylindenyl)zirconium dichloride
dimethylsilanediyl(2-methyl-6-thiapentalene)(2-methyl-4-(4'-tris(trifluoromethyl)methylphenylindenyl)zirconium dichloride
dimethylsilanediyl(2,5-dimethyl-4-thiapentalene)(2-methyl-4-(4'-tris(trifluoromethyl)methylphenylindenyl)zirconium dichloride
dimethylsilanediyl(2,5-dimethyl-6-thiapentalene)(2-methyl-4-(4'-tris(trifluoromethyl)methylphenylindenyl)zirconium dichloride
dimethylsilanediyl(2-methyl-4-oxapentalene)(2-methyl-4-(4'-tris(trifluoromethyl)methylphenylindenyl)zirconium dichloride
dimethylsilanediyl(2-methyl-5-oxapentalene)(2-methyl-4-(4'-tris(trifluoromethyl)methylphenylindenyl) zirconium dichloride
dimethylsilanediyl(2-methyl-6-oxapentalene)(2-methyl-4-(4'-tris(trifluoromethyl)methylphenylindenyl)zirconium dichloride
dimethylsilanediyl(2,5-dimethyl-4-oxapentalene)(2-methyl-4-(4'-tris(trifluoromethyl)methylphenylindenyl)zirconium dichloride
dimethylsilanediyl(2,5-dimethyl-6-oxapentalene)(2-methyl-4-(4'-tris(trifluoromethyl)methylphenylindenyl)zirconium dichloride
dimethylsilanediyl(2-methyl-4-azapentalene)(2-ethyl-4-(4'-tert-butylphenylindenyl)zirconium dichloride
dimethylsilanediyl(2-methyl-5,6-dihydro-4-azapentalene)(2-ethyl-4-(4'-tert-butylphenylindenyl)zirconium dichloride
dimethylsilanediyl(2-methyl-4-azapentalene)(2-ethyl-4-(4'-tert-butylphenyltetrahydroindenyl)zirconium dichloride
dimethylsilanediyl(2-methyl-5-azapentalene)(2-n-butyl-4-(4'-tert-butylphenylindenyl)zirconium dichloride
ethylidene(2-methyl-6-azapentalene)(2-methyl-4-(4'-tert-butylphenylindenyl)zirconium dichloride dimethylsilanediyl(2-methyl-N-trimethylsilyl-4-azapentalene)(2-methyl-4-(4'-tert-butylphenylindenyl)zirconium dichloride
dimethylsilanediyl(2-methyl-N-tolyl-5-azapentalene)(2-n-propyl-4-(4'-tert-butylphenylindenyl)zirconium dichloride
dimethylgermanediyl(2-methyl-N-phenyl-6-azapentalene)(2-methyl-4-(4'-tert-butylphenylindenyl)zirconium dichloride
methylethylidene(2,5-dimethyl-4-azapentalene)(2-methyl-4-(4'-tert-butylphenylindenyl)zirconium dichloride
dimethylsilanediyl(2,5-diisopropyl-6-azapentalene)(2-methyl-4-(4'-tert-butylphenylindenyl)zirconium dichloride
dimethylsilanediyl(2,5-dimethyl-N-phenyl-4-azapentalene)(2,6-dimethyl-4-(4'-tert-butylphenylindenyl)zirconium dichloride
dimethylsilanediyl(2,5-dimethyl-N-phenyl-6-azapentalene)(2-methyl-4-(6'-tert-butylnaphthylindenyl)zirconium dichloride
dimethylsilanediyl(2,5-dimethyl-N-phenyl-6-azapentalene)(2-methyl-4-(6'-tert-butylanthracenylindenyl)zirconium dichloride
dimethylsilanediyl(2-methyl-4-phosphapentalene)(2-methyl-4-(4'-tert-butylphenylindenyl)zirconium dichloride
diphenylsilanediyl(2-methyl-5-thiapentalene)(2-methyl-4-(4'-tert-butylphenylindenyl)zirconium dichloride
methylphenylsilanediyl(2-methyl-6-thiapentalene)(2-methyl-4-(4'-tert-butylphenylindenyl)zirconium dichloride
methylidene(2,5-dimethyl-4-thiapentalene)(2-methyl-4-(4'-tert-butylphenylindenyl)zirconium dichloride
dimethylmethylidene(2,5-dimethyl-6-thiapentalene)(2-methyl-4-(4'-tert-butylphenylindenyl)zirconium dichloride
diphenylsilanediyl(2,5-dimethyl-4-oxapentalene)(2-methyl-4-(4'-tert-butylphenylindenyl)zirconium dichloride
diphenylsilanediyl(2,5-dimethyl-6-oxapentalene)(2-methyl-4-(4'-tert-butylphenylindenyl)zirconium dichloride
dimethylsilanediyl(2-methyl-4-azapentalene)(2-methylindenyl)zirconium dichloride
dimethylsilanediyl(2-methyl-5-azapentalene)(2-methylindenyl)zirconium dichloride
dimethylsilanediyl(2-methyl-6-azapentalene)(2-methylindenyl)zirconium dichloride
dimethylsilanediyl(2-methyl-N-phenyl-4-azapentalene)(2-methylindenyl)zirconium dichloride
dimethylsilanediyl(2-methyl-N-phenyl-5-azapentalene)(2-methylindenyl)zirconium dichloride
dimethylsilanediyl(2-methyl-N-phenyl-6-azapentalene)(2-methylindenyl)zirconium dichloride
dimethylsilanediyl(2,5-dimethyl-4-azapentalene)(2-methylindenyl)zirconium dichloride
dimethylsilanediyl(2,5-dimethyl-6-azapentalene)(2-methylindenyl)zirconium dichloride
dimethylsilanediyl(2,5-dimethyl-N-phenyl-4-azapentalene)(2-methylindenyl)zirconium dichloride
dimethylsilanediyl(2,5-dimethyl-N-phenyl-6-azapentalene)(2-methylindenyl)zirconium dichloride
dimethylsilanediyl(2-methyl-4-thiapentalene)(2-methylindenyl)zirconium dichloride
dimethylsilanediyl(2-methyl-5-thiapentalene)(2-methylindenyl)zirconium dichloride
dimethylsilanediyl(2-methyl-6-thiapentalene)(2-methylindenyl)zirconium dichloride
dimethylsilanediyl(2,5-dimethyl-4-thiapentalene)(2-methylindenyl)zirconium dichloride
dimethylsilanediyl(2,5-dimethyl-6-thiapentalene)(2-methylindenyl)zirconium dichloride
dimethylsilanediyl(2-methyl-4-oxapentalene)(2-methylindenyl)zirconium dichloride
dimethylsilanediyl(2-methyl-5-oxapentalene)(2-methylindenyl)zirconium dichloride
dimethylsilanediyl(2-methyl-6-oxapentalene)(2-methylindenyl)zirconium dichloride
dimethylsilanediyl(2,5-dimethyl-4-oxapentalene)(2-methylindenyl)zirconium dichloride
dimethylsilanediyl(2,5-dimethyl-6-oxapentalene)(2-methylindenyl)zirconium dichloride
dimethylsilanediyl(2-methyl-4-azapentalene)(indenyl)zirconium dichloride
dimethylsilanediyl(2-methyl-5-azapentalene)(indenyl)zirconium dichloride
dimethylsilanediyl(2-methyl-6-azapentalene)(indenyl)zirconium dichloride
dimethylsilanediyl(2-methyl-N-phenyl-4-azapentalene)(indenyl)zirconium dichloride
dimethylsilanediyl(2-methyl-N-phenyl-5-azapentalene)(indenyl)zirconium dichloride
dimethylsilanediyl(2-methyl-N-phenyl-6-azapentalene)(indenyl)zirconium dichloride
dimethylsilanediyl(2,5-dimethyl-4-azapentalene)(indenyl)zirconium dichloride
dimethylsilanediyl(2,5-dimethyl-6-azapentalene)(indenyl)zirconium dichloride
dimethylsilanediyl(2,5-dimethyl-N-phenyl-4-azapentalene)(indenyl)zirconium dichloride
dimethylsilanediyl(2,5-dimethyl-N-phenyl-6-azapentalene)(indenyl)zirconium dichloride
dimethylsilanediyl(2-methyl-4-thiapentalene)(indenyl)zirconium dichloride
dimethylsilanediyl(2-methyl-5-thiapentalene)(indenyl)zirconium dichloride
dimethylsilanediyl(2-methyl-6-thiapentalene)(indenyl)zirconium dichloride
dimethylsilanediyl(2,5-dimethyl-4-thiapentalene)(indenyl)zirconium dichloride
dimethylsilanediyl(2,5-dimethyl-6-thiapentalene)(indenyl)zirconium dichloride
dimethylsilanediyl(2-methyl-4-oxapentalene)(indenyl)zirconium dichloride
dimethylsilanediyl(2-methyl-5-oxapentalene)(indenyl)zirconium dichloride
dimethylsilanediyl(2-methyl-6-oxapentalene)(indenyl)zirconium dichloride
dimethylsilanediyl(2,5-dimethyl-4-oxapentalene)(indenyl)zirconium dichloride
dimethylsilanediyl(2,5-dimethyl-6-oxapentalene)(indenyl)zirconium dichloride
dimethylsilanediyl(2-methyl-4-azapentalene)(2-methyl-4-phenylindenyl)zirconium dichloride
dimethylsilanediyl(2-methyl-5-azapentalene)(2-methyl-4-phenylindenyl)zirconium dichloride
dimethylsilanediyl(2-methyl-6-azapentalene)(2-methyl-4-phenylindenyl)zirconium dichloride
dimethylsilanediyl(2-methyl-N-phenyl-4-azapentalene)(2-methyl-4-phenylindenyl)zirconium dichloride
dimethylsilanediyl(2-methyl-N-phenyl-5-azapentalene)(2-methyl-4-phenylindenyl)zirconium dichloride
dimethylsilanediyl(2-methyl-N-phenyl-6-azapentalene)(2-methyl-4-phenylindenyl)zirconium dichloride
dimethylsilanediyl(2,5-dimethyl-4-azapentalene)(2-methyl-4-phenylindenyl)zirconium dichloride
dimethylsilanediyl(2,5-dimethyl-6-azapentalene)(2-methyl-4-phenylindenyl)zirconium dichloride dimethylsilanediyl(2,5-dimethyl-N-phenyl-4-azapentalene)(2-methyl-4-phenylindenyl)zirconium dichloride
dimethylsilanediyl(2,5-dimethyl-N-phenyl-6-azapentalene)(2-methyl-4-phenylindenyl)zirconium dichloride
dimethylsilanediyl(2-methyl-4-thiapentalene)(2-methyl-4-phenylindenyl)zirconium dichloride
dimethylsilanediyl(2-methyl-5-thiapentalene)(2-methyl-4-phenylindenyl)zirconium dichloride
dimethylsilanediyl(2-methyl-6-thiapentalene)(2-methyl-4-phenylindenyl)zirconium dichloride
dimethylsilanediyl(2,5-dimethyl-4-thiapentalene)(2-methyl-4-phenylindenyl)zirconium dichloride
dimethylsilanediyl(2,5-dimethyl-6-thiapentalene)(2-methyl-4-phenylindenyl)zirconium dichloride
dimethylsilanediyl(2-methyl-4-oxapentalene)(2-methyl-4-phenylindenyl)zirconium dichloride
dimethylsilanediyl(2-methyl-5-oxapentalene)(2-methyl-4-phenylindenyl)zirconium dichloride
dimethylsilanediyl(2-methyl-6-oxapentalene)(2-methyl-4-phenylindenyl)zirconium dichloride
dimethylsilanediyl(2,5-dimethyl-4-oxapentalene)(2-methyl-4-phenylindenyl)zirconium dichloride
dimethylsilanediyl(2,5-dimethyl-6-oxapentalene)(2-methyl-4-phenyl indenyl)zirconium dichloride
dimethylsilanediyl(2-methyl-4-azapentalene)(2-methyl-4,5-benzoindenyl)zirconium dichloride
dimethylsilanediyl(2-methyl-5-azapentalene)(2-methyl-4,5-benzoindenyl)zirconium dichloride
dimethylsilanediyl(2-methyl-6-azapentalene)(2-methyl-4,5-benzoindenyl)zirconium dichloride
dimethylsilanediyl(2-methyl-N-phenyl-4-azapentalene)(2-methyl-4,5-benzoindenyl)zirconium dichloride
dimethylsilanediyl(2-methyl-N-phenyl-5-azapentalene)(2-methyl-4,5-benzoindenyl)zirconium dichloride
dimethylsilanediyl(2-methyl-N-phenyl-6-azapentalene)(2-methyl-4,5-benzoindenyl)zirconium dichloride
dimethylsilanediyl(2,5-dimethyl-4-azapentalene)(2-methyl-4,5-benzoindenyl)zirconium dichloride
dimethylsilanediyl(2,5-dimethyl-6-azapentalene)(2-methyl-4,5-benzoindenyl)zirconium dichloride
dimethylsilanediyl(2,5-dimethyl-N-phenyl-4-azapentalene)(2-methyl-4,5-benzoindenyl)zirconium dichloride
dimethylsilanediyl(2,5-dimethyl-N-phenyl-6-azapentalene)(2-methyl-4,5-benzoindenyl)zirconium dichloride
dimethylsilanediyl(2-methyl-4-thiapentalene)(2-methyl-4,5-benzoindenyl)zirconium dichloride
dimethylsilanediyl(2-methyl-5-thiapentalene)(2-methyl-4,5-benzoindenyl)zirconium dichloride
dimethylsilanediyl(2-methyl-6-thiapentalene)(2-methyl-4,5-benzoindenyl)zirconium dichloride
dimethylsilanediyl(2,5-dimethyl-4-thiapentalene)(2-methyl-4,5-benzoindenyl)zirconium dichloride
dimethylsilanediyl(2,5-dimethyl-6-thiapentalene)(2-methyl-4,5-benzoindenyl)zirconium dichloride
dimethylsilanediyl(2-methyl-4-oxapentalene)(2-methyl-4,5-benzoindenyl)zirconium dichloride
dimethylsilanediyl(2-methyl-5-oxapentalene)(2-methyl-4,5-benzoindenyl)zirconium dichloride
dimethylsilanediyl(2-methyl-6-oxapentalene)(2-methyl-4,5-benzoindenyl)zirconium dichloride
dimethylsilanediyl(2,5-dimethyl-4-oxapentalene)(2-methyl-4,5-benzoindenyl)zirconium dichloride
dimethylsilanediyl(2,5-dimethyl-6-oxapentalene)(2-methyl-4,5-benzoindenyl)zirconium dichloride
dimethylsilanediylbis(2-methyl-4-azapentalene)zirconium dichloride
dimethylsilanediylbis(2-methyl-5-azapentalene)zirconium dichloride
dimethylsilanediylbis(2-methyl-6-azapentalene)zirconium dichloride
dimethylsilanediylbis(2-methyl-N-phenyl-4-azapentalene)zirconium dichloride
dimethylsilanediylbis(2-methyl-N-phenyl-5-azapentalene)zirconium dichloride
dimethylsilanediylbis(2-methyl-N-phenyl-6-azapentalene)zirconium dichloride
dimethylsilanediylbis(2,5-dimethyl-4-azapentalene)zirconium dichloride
dimethylsilanediylbis(2,5-dimethyl-6-azapentalene)zirconium dichloride
dimethylsilanediylbis(2,5-dimethyl-N-phenyl-4-azapentalene)zirconium dichloride
dimethylsilanediylbis(2,5-dimethyl-N-phenyl-6-azapentalene)zirconium dichloride
dimethylsilanediylbis(2-methyl-4-thiapentalene)zirconium dichloride
dimethylsilanediylbis(2-methyl-5-thiapentalene)zirconium dichloride
dimethylsilanediylbis(2-methyl-6-thiapentalene)zirconium dichloride
dimethylsilanediylbis(2,5-dimethyl-4-thiapentalene)zirconium dichloride
dimethylsilanediylbis(2,5-dimethyl-6-thiapentalene)zirconium dichloride
dimethylsilanediylbis(2-methyl-4-oxapentalene)zirconium dichloride
dimethylsilanediylbis(2-methyl-5-oxapentalene)zirconium dichloride
dimethylsilanediylbis(2-methyl-6-oxapentalene)zirconium dichloride
dimethylsilanediylbis(2,5-dimethyl-4-oxapentalene)zirconium dichloride
dimethylsilanediylbis(2,5-dimethyl-6-oxapentalene)zirconium dichloride Further examples of metallocenes which can be used in the process of the present invention are metallocenes from the above list in which the zirconium fragment "-zirconium dichloride" is replaced by
zirconium monochloride mono(2,4-di-tert-butylphenoxide)
zirconium monochloride mono(2,6-di-tert-butylphenoxide)
zirconium monochloride mono(3,5-di-tert-butylphenoxide)
zirconium monochloride mono(2,6-di-sec-butylphenoxide)
zirconium monochloride mono(2,4-dimethylphenoxide)
zirconium monochloride mono(2,3-dimethylphenoxide)
zirconium monochloride mono(2,5-dimethylphenoxide)
zirconium monochloride mono(2,6-dimethylphenoxide)
zirconium monochloride mono(3,4-dimethylphenoxide)
zirconium monochloride mono(3,5-dimethylphenoxide)
zirconium monochloride monophenoxide
zirconium monochloride mono(2-methylphenoxide)
zirconium monochloride mono(3-methylphenoxide)
zirconium monochloride mono(4-methylphenoxide)
zirconium monochloride mono(2-ethylphenoxide)
zirconium monochloride mono(3-ethylphenoxide)
zirconium monochloride mono(4-ethylphenoxide)
zirconium monochloride mono(2-sec-butylphenoxide)
zirconium monochloride mono(2-tert-butylphenoxide)
zirconium monochloride mono(3-tert-butylphenoxide)
zirconium monochloride mono(4-sec-butylphenoxide)
zirconium monochloride mono(4-tert-butylphenoxide)
zirconium monochloride mono(2-isopropyl-5-methylphenoxide)

zirconium monochloride mono(4-isopropyl-3-methylphenoxide)
zirconium monochloride mono(5-isopropyl-2-methylphenoxide)
zirconium monochloride mono(5-isopropyl-3-methylphenoxide)
zirconium monochloride mono(2,4-bis-(2-methyl-2-butyl)phenoxide)
zirconium monochloride mono(2,6-di-tert-butyl-4-methylphenoxide)
zirconium monochloride mono(4-nonylphenoxide)
zirconium monochloride mono(1-naphthoxide)
zirconium monochloride mono(2-naphthoxide)
zirconium monochloride mono(2-phenylphenoxide)
zirconium monochloride mono(tert-butoxide)
zirconium monochloride mono(N-methylanilide)
zirconium monochloride mono(2-tert-butylanilide)
zirconium monochloride mono(tert-butylamide)
zirconium monochloride mono(di-isopropylamide)
zirconium monochloride monomethyl
zirconium monochloride monobenzyl
zirconium monochloride mononeopentyl.

Also preferred are the corresponding dimethyl zirconium compounds and the corresponding zirconium-$\eta^4$-butadiene compounds.

The preferred catalyst system of the present invention comprises at least one main group alkyl B), where B) is particularly preferably a compound of the formula (V), usually an organometallic compound, which can be reacted in any stoichiometric ratio with compounds of the formula (III) and (IV).

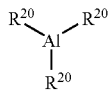
(V)

The radicals $R^{20}$ in formula (V) can be identical or different and are each a halogen atom, a hydrogen atom, a $C_1$–$C_{40}$ group, preferably $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl. $R^{20}$ are preferably $C_1$–$C_6$-alkyl groups, particularly preferably $C_1$–$C_4$-alkyl groups.

For the reaction of compounds of the formula (III) and (IV) with compounds of the formula (V), the compounds can be dissolved or suspended in a solvent. However, the reaction can also be carried out in the absence of solvent or suspension medium. Suitable solvents are those described above; preference is given to using the same solvent. The reaction is generally carried out for from 1 minute to 96 hours, preferably from 10 minutes to 8 hours. The temperature of the initial charge during the addition is from −100° C. to 200° C., preferably from −80° C. to 150° C., particularly preferably from 20° C. to 150° C. The temperature is selected so that at least one reactant is present in a liquid phase. The subsequent reaction temperature is preferably in a range from 20° C. to 150° C. Furthermore, the reaction can be carried out under atmospheric pressure or under superatmospheric pressure, but the latter requires appropriate reactors. The molar ratio in which the compounds of the formula (III) and (IV) are combined with the chemical compound of the formula (V) is from 1000:1 to 0.01:1, based on the amount of $M^3$ or $M^4$ in the compounds of the formulae (III) and (IV) used.

Preference is given to a molar ratio of compounds of the formulae (III) and (IV) to the chemical compound of the formula (V) of from 100:1 to 1:1, based on the amount of $M^3$ or $M^4$ in the compounds of the formulae (III) and (IV) used.

In the preparation of the catalyst system of the present invention, a molar ratio of aluminum in the compounds of the formula (III) to $M^4$ in the compounds of the formula (IV) of from 10,000 to 0.01 is employed. Preference is given to using a molar ratio of from 1000 to 0.1, very particularly preferably from 100 to 1. For this purpose, a compound of the formula (V) can be additionally added in a molar ratio of Al:$M^4$ of from 10,000 to 0.01. Preference is given to using a molar ratio of from 1000 to 0.1, very particularly preferably from 100 to 1.

The compounds can be brought into contact with one another in any conceivable combination. One possible method is to dissolve or suspend an organic transition metal compound of the formula (IV) in an aliphatic or aromatic solvent such as toluene, heptane, tetrahydrofuran or diethyl ether. A compound of the formula (V) is then added in dissolved or suspended form. The reaction time is from 1 minute to 24 hours, preferably from 5 minutes to 120 minutes. The reaction temperature is from −10° C. to +200° C., preferably from 0° C. to 50° C. Subsequently, an organoaluminum compound of the formula (III) is added either as such or in dissolved or suspended form. The reaction time is from 1 minute to 24 hours, preferably from 5 minutes to 120 minutes. The reaction temperature is from −10° C. to +200° C., preferably from 0° C. to 50° C. The individual components can also be introduced successively, in any order, into the polymerization vessel.

If desired, the catalyst system of the present invention can also be used in supported form. For this purpose, the catalyst system of the present invention can be reacted with a support component.

The preferred catalyst system of the present invention comprises a support component C) which may be any organic or inorganic, inert solid. Particular preference is given to porous supports such as talc, inorganic oxides, mixed oxides and finely divided polymer powders (e.g. polyolefins).

Suitable inorganic oxides may be found among the oxides of elements of main groups II–VI and transition groups III–IV of the Periodic Table of the Elements. Examples of oxides preferred as supports include silicon dioxide, aluminum oxide and also mixed oxides of the two elements and corresponding oxide mixtures. Other inorganic oxides which can be used either alone or in combination with the above-mentioned preferred oxidic supports are, for example, MgO, $ZrO_2$, $TiO_2$ or $B_2O_3$.

The support materials used generally have a specific surface area in the range from 10 to 1000 m$^2$/g, a pore volume in the range from 0.1 to 5 ml/g and a mean particle size of from 1 to 500 μm. Preference is given to supports having a specific surface area in the range from 50 to 500 μm, a pore volume in the range from 0.5 to 3.5 ml/g and a mean particle size in the range from 5 to 350 μm. Particular preference is given to supports having a specific surface area in the range from 200 to 400 m$^2$/g, a pore volume in the range from 0.8 to 3.0 ml/g and a mean particle size of from 10 to 200 μm.

If the support material used naturally has a low moisture content or residual solvent content, dehydration or drying before use can be omitted. If this is not the case, for example when using silica gel as support material, dehydration or drying is advisable. Thermal dehydration or drying of the support material can be carried out under reduced pressure with simultaneous inert gas blanketing (e.g. nitrogen). The drying temperature is in the range from 100 to 1000° C., preferably from 200 to 800° C. In this case, the parameter pressure is not critical. The duration of the drying process can be from 1 to 24 hours. Shorter or longer drying times are possible, provided that equilibrium with the hydroxyl groups on the support surface can be established under the conditions selected, which normally takes from 4 to 8 hours.

Dehydration or drying of the support material can also be carried out by chemical means, by reacting the adsorbed water and the hydroxyl groups on the surface with suitable passivating agents. The reaction with the passivating reagent can convert the hydroxyl groups fully or partly into a form which leads to no adverse interaction with the catalytically active centers. Suitable passivating agents are, for example, silicon halides and silanes, e.g. silicon tetrachloride, chlorotrimethylsilane, dimethylaminotrichlorosilane, or organometallic compounds of aluminum, boron and magnesium, for example trimethylaluminum, triethylaluminum, triisobutylaluminum, triethylborane, dibutylmagnesium. Chemical dehydration or passivation of the support material is carried out, for example, by reacting a suspension of the support material in a suitable solvent with the passivating reagent in pure form or as a solution in a suitable solvent in the absence of air and moisture. Suitable solvents are, for example, aliphatic or aromatic hydrocarbons such as pentane, hexane, heptane, toluene or xylene. Passivation is generally carried out at from 25° C. to 120° C., preferably from 50° C. to 70° C. The reaction time is from 30 minutes to 20 hours, preferably from 1 to 5 hours. After chemical dehydration is complete, the support material can be isolated by filtration under inert conditions, washed one or more times with suitable inert solvents as described above and subsequently dried in a stream of inert gas or under reduced pressure.

Organic support materials such as finely divided polyolefin powders (e.g. polyethylene, polypropylene or polystyrene) can also be used and should likewise be free of adhering moisture, solvent residues or other impurities by appropriate purification and drying operations before use.

To apply the catalyst system of the present invention to a support, the catalyst mixture prepared above is mixed with a dehydrated or passivated support material, the solvent is removed and the resulting supported metallocene catalyst system is dried in order to ensure that all or most of the solvent is removed from the pores of the support material. The supported catalyst is obtained as a free-flowing powder.

The present invention also provides a process for preparing a polyolefin by polymerization of one or more olefins in the presence of the catalyst system of the present invention, preferably comprising at least one organometallic component of the formula (V). For the purposes of the present invention, the term polymerization encompasses both homopolymerization and copolymerization.

Preference is given to polymerizing olefins of the formula $R_m$—CH═CH—$R_n$, where $R_m$ and $R_n$ are identical or different and are each a hydrogen atom or an organic radical having from 1 to 20 carbon atoms, in particular from 1 to 10 carbon atoms, and $R_m$ and $R_n$ together with the atoms connecting them may also form one or more rings.

Examples of such olefins are 1-olefins having 2–40, preferably 2–10, carbon atoms, e.g. ethene, propene, 1-butene, 1-pentene, 1-hexene, 4-methyl-1-pentene or 1-octene, styrene, dienes such as 1,3-butadiene, 1,4-hexadiene, vinylnorbornene, norbornadiene or ethylnorbornadiene and cyclic olefins such as norbornene, tetracyclododecene or methylnorbornene. In the process of the present invention, preference is given to homopolymerizing propene or ethene or copolymerizing propene with ethene and/or with one or more 1-olefins having from 4 to 20 carbon atoms, e.g. hexene, and/or one or more dienes having from 4 to 20 carbon atoms, e.g. 1,4-butadiene, norbornadiene, ethylidenenorbornene or ethylnorbornadiene. Examples of corresponding copolymers are ethene-propene copolymers or ethene-propene-1,4-hexadiene terpolymers.

The polymerization is carried out at from −60° C. to 300° C., preferably from 50° C. to 200° C., very particularly preferably from 50° C.-80° C. The pressure is from 0.5 to 2000 bar, preferably from 5 to 64 bar.

The polymerization can be carried out in solution, in bulk, in suspension or in the gas phase, continuously or batchwise, in one or more stages.

The catalyst system prepared according to the present invention can be used as sole catalyst component for the polymerization of olefins having from 2 to 20 carbon atoms, or preferably in combination with at least one alkyl compound of elements of main groups I to III of the Periodic Table, e.g. an aluminum alkyl, magnesium alkyl or lithium alkyl or an aluminoxane. The alkyl compound is added to the monomer or suspension medium and serves to purify the monomer of substances which can impair the catalyst activity. The amount of alkyl compound added depends on the quality of the monomers used.

As molar mass regulator and/or to increase the activity, hydrogen is added if necessary.

The supported catalyst system can be used directly for the polymerization. However, it is also possible to remove the solvent and then to resuspend the catalyst system for use in the polymerization. The advantage of this activation method is that it offers the option of forming the polymerization-active catalyst system only in the reactor. This prevents partial decomposition from occurring during introduction of the air-sensitive catalyst.

Furthermore, an additive such as an antistatic can be used according to the present invention, e.g. for improving the particle morphology of the polymer.

It is generally possible to use all antistatics which are suitable for polymerization. Examples are salt mixtures of calcium salts of Medialan acid and chromium salts of N-stearylanthranilic acid, as described in DE-A-3,543,360. Further suitable antistatics are, for example, $C_{12}$- to $C_{22}$-fatty acid soaps of alkali metals or alkaline earth metals, salts of sulfonic esters, esters of polyethylene glycols with fatty acids, polyoxyethylene alkyl ethers, etc. An overview of antistatics is given in EP-A-0,107,127.

It is also possible to use a mixture of a metal salt of Medialan acid, a metal salt of anthranilic acid and a polyamine as antistatic, as described in EP-A-0,636,636.

Commercially available products such as Stadis® 450 from DuPont, namely a mixture of toluene, isopropanol, dodecylbenzenesulfonic acid, a polyamine, a copolymer of 1-decene and $SO_2$ and also 1-decene, or ASA®-3 from Shell and ARU5R® 163 from ICI can likewise be used.

The antistatic is preferably used as a solution; in the preferred case of Stadis® 450, preference is given to using from 1 to 50% by weight, more preferably from 5 to 25% by weight, of this solution, based on the mass of the supported catalyst used (support together with covalently bound metallocenium-forming compound and one or more metallocene compounds, e.g. of the formula (IV)). However, the amounts of antistatic required fluctuate within a wide range depending on the type of antistatic used.

The polymers prepared using the catalyst system of the present invention display a uniform particle morphology and contain no fines. No deposits or cake material are formed in the polymerization using the catalyst system of the present invention.

The polymers prepared by the process of the present invention are particularly useful for producing hard and stiff shaped bodies having a good tensile strength, e.g. fibers, filaments, injection-molded parts, films, sheets or large hollow bodies (e.g. pipes).

The preparation, which has been described in general terms above, of a catalyst system according to the present invention can be carried out by two different methods based on either physisorption or covalent bonding to the support. The sequence of steps employed in the two methods is described below:

Method 1 (Physisorption):

In step 1, an inorganic support material (C) is reacted with a metal compound of the formula (V). The metal compound of the formula (V) is preferably added as a solution to a suspension of the support. Solvents or suspension media which can be used are those described under B. The amount of metal compounds of the formula (V) can vary within wide limits; the minimum amount depends on the number of hydroxyl groups on the support. Temperature, reaction times and pressures are not critical per se; preference is given to the temperatures and reaction times described under Method 2. After pretreatment of the support, it has been found to be useful to remove the excess metal compound of the formula (V) by washing, for example with hydrocarbons such as pentane, hexane, ethylbenzene or heptane, and to dry the support.

This material is then reacted in step 2 with a metallocene complex of the formula (IV) and one or more of the compounds of the present invention, which preferably comprise compounds of the formula III. It is also possible to use mixtures of various metallocene complexes.

The conditions for the reaction of the metallocene complex with the compound of the present invention are not critical per se; the reaction is preferably carried out in solution, especially in hydrocarbons as solvents, preferably aromatic hydrocarbons such as toluene.

An amount of from 0.1 to 10% by weight of metallocene complex, based on the inorganic support material, is particularly useful. The conditions for this reaction are likewise not critical. Temperatures in the range from 20 to 80° C. and reaction times in the range from 0.1 to 20 hours have been found to be particularly useful.

In a further step 3, the material obtained after step 2 is reacted with a metal compound of the formula (V). This activation can be carried out at any point in time, i.e. before, during or after the material obtained in step 2 is introduced into the reactor. The activation is preferably carried out after the material obtained in step 2 has been introduced into the reactor.

The chemical products of the present invention, in particular those comprising compounds of the formula (III), display, in particular, a high activity when used as cocatalysts in the polymerization of olefins. In addition, they can be stored for a long time; they are not pyrophoric and are readily soluble.

Method 2 (Covalent Bonding to a Support)

The catalyst system of the present invention can further comprise a Lewis base of the formula (VI)

$$M^6R^{21}R^{22}R^{23} \quad \text{(VI)}$$

where $M^6$ is an element of main group V of the Periodic Table of the Elements, $R^{21}$, $R^{22}$, $R^{23}$ are identical or different and are each a hydrogen atom or a $C_1$–$C_{20}$-alkyl, $C_1$–$C_{20}$-haloalkyl, $C_6$–$C_{40}$-aryl, $C_6$–$C_{40}$-haloaryl, $C_7$–$C_{40}$-alkylaryl or $C_7$–$C_{40}$-arylalkyl group, where two radicals or all three radicals $R^{21}$, $R^{22}$ and $R^{23}$ may be joined via $C_2$–$C_{20}$ units, where at least one radical $R^{21}$, $R^{22}$ or $R^{23}$ is not a hydrogen atom or a linear alkyl chain.

Preference is given to Lewis bases of the formula (VI) in which $R^{21}$, $R^{22}$ and $R^{23}$ are identical or different and are each a hydrogen atom or a $C_1$–$C_{20}$-alkyl, $C_1$–$C_{20}$-haloalkyl, $C_6$–$C_{40}$-aryl, $C_6$–$C_{40}$-haloaryl, $C_7$–$C_{40}$-alkylaryl or $C_7$–$C_{40}$-arylalkyl group, where two radicals or all three radicals $R^{21}$, $R^{22}$ and $R^{23}$ may be joined via $C_2$–$C_{20}$ units and at least one radical $R^{21}$, $R^{22}$ and $R^{23}$ is a radical having from 2 to 20 carbon atoms or an aromatic group, each of which may be substituted and/or contain heteroatoms selected from the group consisting of P, O, S, N. It is preferred that at least one radical $R^{21}$, $R^{22}$ and $R^{23}$ is an alkylaryl group, in particular a benzylic group.

$M^6$ is preferably nitrogen.

Nonlimiting examples of Lewis bases of the formula (VI) are:

N,N-dimethylcyclohexylamine, N,N-diethylcyclohexylamine, N,N-dimethylisopropylamine, N,N-diethylbenzylamine, N,N-dimethyl-p-toluidine, N,N-diethyl-p-toluidine, N,N-dimethylbenzylamine, N,N-diethylisopropylamine, N,N-diisopropylmethylamine, N,N-diisopropylethylamine, N,N-dimethylcyclopentylamine, N,N-dimethylcycloheptenylamine, N,N-dimethylcyclooctanylamine, N,N-dimethylnonanoylamine, N,N-diethylcyclopentylamine, N,N-diethylcycloheptenylamine, N,N-diethylcyclooctanylamine, N,N-diethylnonanoylamine;

N-benzyldimethylamine, N-benzyldiethylamine, N-benzylbutylamine, N-benzyl-tert-butylamine, N'-benzyl-N,N-dimethylethylenediamine, N-benzylethylenediamine, N-benzylisopropylamine, N-benzylmethylamine, N-benzylethylamine, N-benzyl-l-phenylethylamine, N-benzyl-2-phenylethylamine, or N-benzylpiperazine;

N,N-dimethylisopropylamine, N,N-dimethyl-2-butylamine, N,N-dimethylisobutylamine, N,N-dimethyl-2-pentylamine, N,N-dimethyl-3-pentylamine, N,N-dimethyl-2-methylbutylamine, N,N-dimethyl-3-methylbutylamine, N,N-dimethylcyclopentylamine, N,N-dimethyl-2-hexylamine, N,N-dimethyl-3-hexylamine, N,N-dimethyl-2-methylpentylamine, N,N-dimethyl-3-methylpentylamine, N,N-dimethyl-4-methylpentylamine, N,N-dimethyl-2-ethylbutylamine, N,N-dimethylcyclohexylamine, N,N-dimethyl-2-heptylamine, N,N-dimethyl-3-heptylamine, N,N-dimethyl-4-heptylamine, N,N-dimethyl-2-methylhexylamine, N,N-dimethyl-3-methylhexylamine, N,N-dimethyl-4-methylhexylamine, N,N-dimethyl-5-methylhexylamine, N,N-dimethyl-2-ethylpentylamine, N,N-dimethyl-3-ethylpentylamine, N,N-dimethyl-2-propylbutylamine, N,N-dimethylcycloheptylamine, N,N-dimethylmethylcyclohexylamine, N,N-dimethylbenzylamine, N,N-dimethyl-2-octylamine, N,N-dimethyl-3-octylamine;

N,N-dimethyl-4-octylamine, N,N-dimethyl-2-methylheptylamine, N,N-dimethyl-3-methylheptylamine, N,N-dimethyl-4-methylheptylamine, N,N-dimethyl-5-methylheptylamine, N,N-dimethyl-6-methylheptylamine, N,N-dimethyl-2-ethylhexylamine, N,N-dimethyl-3-ethylhexylamine, N,N-dimethyl-4-ethylhexylamine, N,N-dimethyl-2-propylpentylamine, N,N-dimethylcyclooctylamine, N,N-dimethyldimethylcyclohexylamine, N,N-diethylisopropylamine, N,N-diethyl-2-butylamine, N,N-diethylisobutylamine, N,N-diethyl-2-pentylamine, N,N-diethyl-3-pentylamine, N,N-diethyl-2-methylbutylamine, N,N-diethyl-3-methylbutylamine, N,N-diethylcyclopentylamine, N,N-diethyl-2-hexylamine, N,N-diethyl-3-hexylamine, N,N-diethyl-2-methylpentylamine, N,N-diethyl-3-methylpentylamine, N,N-diethyl-4-methylpentylamine, N,N-diethyl-2-ethylbutylamine, N,N-diethylcyclohexylamine, N,N-diethyl-2-heptylamine, N,N-diethyl-3-heptylamine, N,N-diethyl-4-heptylamine, N,N-diethyl-2-methylhexylamine, N,N-diethyl-3-methylhexylamine, N,N-diethyl-4-methylhexylamine, N,N-diethyl-5-methylhexylamine, N,N-diethyl-2-ethylpentylamine, N,N-diethyl-3-ethylpentylamine, N,N-diethyl-2-propylbutylamine, N,N-diethylcycloheptylamine, N,N-diethylmethylcyclohexylamine, N,N-diethylbenzylamine, N,N-diethyl-2-octylamine, N,N-diethyl-3-octylamine, N,N-diethyl-4-octylamine, N,N-diethyl-2-methylheptylamine, N,N-diethyl-3-methylheptylamine, N,N-diethyl-4-methylheptylamine, N,N-diethyl-5-methylheptylamine, N,N-diethyl-6-methylheptylamine, N,N-diethyl-2-ethylhexylamine, N,N-diethyl-3-ethylhexylamine, N,N-diethyl-4-ethylhexylamine, N,N-diethyl-2-propylpentylamine, N,N-diethylcyclooctylamine, N,N-diethyldimethylcyclohexylamine, N-methyl-N-ethyl-isopropylamine, N-methyl-N-ethyl-2-butylamine, N-methyl-N-ethylisobutylamine, N-methyl-N-ethyl-2-pentylamine, N-methyl-N-ethyl-3-pentylamine, N-methyl-N-ethyl-2-methylbutylamine, N-methyl-N-ethyl-3-methylbutylamine, N-methyl-N-ethylcyclopentylamine, N-methyl-N-ethyl-2-hexylamine, N-methyl-N-ethyl-3-hexylamine, N-methyl-N-ethyl-2-methylpentylamine, N-methyl-N-ethyl-3-methylpentylamine, N-methyl-N-ethyl-4-methylpentylamine, N-methyl-N-ethyl-2-ethylbutylamine, N-methyl-N-ethylcyclohexylamine, N-methyl-N-ethyl-2-heptylamine, N-methyl-N-ethyl-3-heptylamine;

N-methyl-N-ethyl-4-heptylamine, N-methyl-N-ethyl-2-methylhexylamine;

N-methyl-N-ethyl-3-methylhexylamine, N-methyl-N-ethyl-4-methylhexylamine, N-methyl-N-ethyl-5-methylhexylamine, N-methyl-N-ethyl-2-ethylpentylamine, N-methyl-N-ethyl-3-ethylpentylamine, N-methyl-N-ethyl-2-propylbutylamine, N-methyl-N-ethylcycloheptylamine, N-methyl-N-ethylmethylcyclohexylamine, N-methyl-N-ethylbenzylamine, N-methyl-N-ethyl-2-octylamine, N-methyl-N-ethyl-3-octylamine, N-methyl-N-ethyl-4-octylamine, N-methyl-N-ethyl-2-methylheptylamine, N-methyl-N-ethyl-3-methylheptylamine, N-methyl-N-ethyl-4-methylheptylamine, N-methyl-N-ethyl-5-methylheptylamine, N-methyl-N-ethyl-6-methylheptylamine, N-methyl-N-ethyl-2-ethylhexylamine, N-methyl-N-ethyl-3-ethylhexylamine, N-methyl-N-ethyl-4-ethylhexylamine, N-methyl-N-ethyl-2-propylpentylamine, N-methyl-N-ethylcyclooctylamine, N-methyl-N-ethyldimethylcyclohexylamine, N-methyldiisopropylamine, N-methylbis(2-butyl)amine, N-methylbis(isobutyl)amine, N-methylbis(2-pentyl)amine, N-methylbis(3-pentyl)amine, N-methylbis(2-methylbutyl)amine, N-methylbis(3-methylbutyl)amine, N-methyldicyclopentylamine, N-methylbis(2-hexyl)amine, N-methylbis(3-hexyl)amine, N-methylbis(2-methylpentyl)amine, N-methylbis(3-methylpentyl)amine, N-methylbis(4-methylpentyl)amine, N-methylbis(2-ethylbutyl)amine, N-methyldicyclohexylamine, N-methylbis (2-heptyl)amine, N-methylbis(3-heptyl)amine, N-methylbis(4-heptyl)amine, N-methylbis(2-methylhexyl)amine, N-methylbis(3-methylhexyl)amine, N-methylbis(4-methylhexyl)amine, N-methylbis(5-methylhexyl)amine, N-methylbis(2-ethylpentyl)amine, N-methylbis(3-ethylpentyl)amine, N-methylbis(2-propylbutyl)amine, N-methylbis(cycloheptyl)amine, N-methylbis(methylcyclohexyl)amine, N-methyldibenzylamine, N-methylbis(2-octyl)amine, N-methylbis(3-octyl)amine, N-methylbis(4-octyl)amine, N-methylbis(2-methylheptyl)amine, N-methylbis(3-methylheptyl)amine, N-methylbis(4-methylheptyl)amine, N-methylbis(5-methylheptyl)amine, N-methylbis(6-methylheptyl)amine, N-methylbis(2-ethylhexyl)amine, N-methylbis(3-ethylhexyl)amine, N-methylbis(4-ethylhexyl)amine, N-methylbis(2-propylpentyl)amine, N-methylbis(cyclooctyl)amine, N-methylbis(dimethylcyclohexyl)amine, N-ethyldiisopropylamine, N-ethylbis(2-butyl)amine, N-ethylbis(isobutyl)amine, N-ethylbis(2-pentyl)amine, N-ethylbis(3-pentyl)amine, N-ethylbis(2-methylbutyl)amine, N-ethylbis(3-methylbutyl)amine, N-ethyldicyclopentylamine, N-ethylbis(2-hexyl)amine, N-ethylbis(3-hexyl)amine, N-ethylbis(2-methylpentyl)amine, N-ethylbis(3-methylpentyl)amine, N-ethylbis(4-methylpentyl)amine, N-ethylbis(2-ethylbutyl)amine, N-ethyldicyclohexylamine, N-ethylbis(2-heptyl)amine, N-ethylbis(3-heptyl)amine, N-ethylbis(4-heptyl)amine, N-ethylbis(2-methylhexyl)amine, N-ethylbis(3-methylhexyl)amine, N-ethylbis(4-methylhexyl)amine, N-ethylbis(5-methylhexyl)amine, N-ethylbis(2-ethylpentyl)amine, N-ethylbis(3-ethylpentyl)amine, N-ethylbis(2-propylbutyl)amine, N-ethylbis(cycloheptyl)amine, N-ethylbis(methylcyclohexyl)amine, N-ethyldi(benzyl)amine, N-ethylbis(2-octyl)amine, N-ethylbis(3-octyl)amine, N-ethylbis(4-octyl)amine, N-ethylbis(2-methylheptyl)amine, N-ethylbis(3-methylheptyl)amine, N-ethylbis(4-methylheptyl)amine, N-ethylbis(5-methylheptyl)amine, N-ethylbis(6-methylheptyl)amine, N-ethylbis(2-ethylhexyl)amine, N-ethylbis(3-ethylhexyl)amine, N-ethylbis(4-ethylhexyl)amine, N-ethylbis(2-propylpentyl)amine, N-ethylbis(cyclooctyl)amine, N-ethylbis(dimethylcyclohexyl)amine.

In step 1 of Method 2, an inorganic support material (C) is reacted with a Lewis base of the formula (VI). The Lewis base of the formula (VI) is preferably added as a solution to a suspension of the support. Suitable solvents or suspension media are, in particular, hydrocarbons, preferably aromatic hydrocarbons such as toluene. The amount of Lewis base of the formula (VI) can vary within wide limits; the minimum amount depends on the number of hydroxyl groups on the support. It has also been found to be useful for, after the pretreatment of the support, the support material to be used moist in step 2.

This material is then reacted in step 2 with one or more of the chemical compounds of the present invention, which preferably comprise compounds of the formula (III). It has been found to be useful, after step 2, to remove excess Lewis base of the formula (VI) by washing, for example with hydrocarbons such as pentane, hexane, ethylbenzene or heptane, and to dry the support.

The covalently supported cocatalyst prepared in this way is, in step 3, brought into contact with a reaction mixture comprising the organometallic compound of the formula (IV) and an aluminum alkyl of the formula (V). The reaction is preferably carried out in solution, especially in hydrocarbons as solvents, preferably aromatic hydrocarbons such as toluene.

An amount of from 0.1 to 10% by weight of metallocene complex, based on the inorganic support material, is particularly useful.

The conditions for the reactions in steps 1 to 3 are not critical; temperatures within the range from 20 to 150° C. and reaction times in the range from 0.1 to 20 hours have been found to be particularly suitable.

The catalyst material prepared in this way is filtered off, if desired washed with hydrocarbons such as pentane, hexane, ethylbenzene or heptane and dried to constant weight.

The following examples serve to illustrate the invention. In the examples, preparation and handling of the compounds was carried out in the absence of air and moisture under argon (Schlenk technique). All solvents required were dried before use by boiling for a number of hours over suitable desiccants and subsequent distillation under argon. For characterization of the compounds, samples were taken from the individual reaction mixtures and dried in an oil pump vacuum.

EXAMPLES

A) Preparation of the Novel Chemical Products Suitable as Cocatalysts and Preparation/Description of the Cocatalysts Used for Comparison

Example 1

Cocatalyst (1)

5.0 ml of trimethylaluminum (2M in Exxol, viz. a hydrocarbon mixture from Exxon; 5.4 mmol) together with 100 ml of toluene were placed in a reaction vessel. 3.65 g (5.4 mmol) of 4,4'-dihydroxyoctafluorobiphenyl monohydrate were added to this solution. The reaction solution was stirred at 60° C. for one hour. The chemical product 1 obtained was subsequently used without purification for application to a support.

Example 2

Cocatalyst (2)

8.0 ml of triethylaluminum (2M in Exxol, 5.4 mmol) together with 100 ml of toluene were placed in a reaction vessel. 3.65 g (5.4 mmol) of 4,4'-dihydroxyoctafluorobiphenyl monohydrate were added to this solution. The reaction solution was stirred at 60° C. for one hour. The chemical product 2 was subsequently used without purification for application to a support.

Example 3

Cocatalyst (3)

7.7 ml of triisobutylaluminum (2M in Varsol, viz. a hydrocarbon mixture from Exxon; 5.4 mmol) together with 100 ml of toluene were placed in a reaction vessel. 3.65 g (5.4 mmol) of 4,4'-dihydroxyoctafluorobiphenyl monohydrate were added to this solution. The reaction solution was stirred at 60° C. for one hour. Chemical product 3 obtained was subsequently used without purification for application to a support.

Comparative Example 1

Cocatalyst (4)

30% strength methylaluminoxane solution (Albemarle Corporation, Baton Rouge, La., USA)

Comparative Example 2

Cocatalyst (5) (No Prior Art)

10 ml of a solution of trimethylaluminum (TMA) in toluene (2 mol/l) were added dropwise at room temperature to a suspension of 20 mmol of dihydroxyoctafluorobiphenyl. The mixture was subsequently stirred at room temperature for 3 hours. As reaction product, a 1:1 condensate of TMA and dihydroxyoctafluorobiphenyl was obtained.

B) Preparation of the Supported Cocatalysts 14.0 g of $SiO_2$ (XPO 2107, from Grace, dried at 600° C. in a stream of argon) together with 20 ml of toluene were placed in a reaction vessel, 2.6 ml of N,N-dimethylaniline (20.80 mmol) were added dropwise and the mixture was stirred at room temperature for 2 hours. Subsequently, at 0° C., 20.80 mmol of the respective cocatalysts 1–3, in each case dissolved in 40 ml of toluene, were added. The suspension was allowed to warm to room temperature and was stirred for two hours at this temperature. The resulting bluish suspension was filtered and the residue was washed with 50 ml of toluene and subsequently with 3×10 ml of n-pentane. The residue was then dried in an oil pump vacuum. This in each case gave the supported cocatalyst system which was weighed.

C) Preparation of Catalyst Systems

Catalyst systems according to the present invention 0.30 ml of trimethylaluminum (20% strength in Exxol, 700 µmol) was added to a solution of 50 mg (80 µmol) of dimethylsilanediylbis(2-methyl-4-phenylindenyl)zirconium dichloride in 50 ml of toluene and the solution was stirred at room temperature for 1.5 hours. 1920 µmol/g [$SiO_2$] of the supported cocatalysts 1 to 3 from B were subsequently added a little at a time. The solution was stirred at room temperature for 60 minutes. The solvent was then removed in an oil pump vacuum, giving in each case a light-red free-flowing powder.

Comparison:

Dimethylsilanediylbis(2-methyl-4-phenylindenyl)zirconium dichloride/MAO System 0.30 ml of trimethylaluminum (20% strength in Exxol, 700 µmol) was added to a solution of 50 mg (80 µmol) of dimethylsilanediylbis(2-methyl-4-phenylindenyl)zirconium dichloride in 50 ml of toluene and the solution was stirred at room temperature for 1.5 hours. 1920 µmol/g [$SiO_2$] of a 30% strength methylaluminoxane solution in toluene (Albermarle Corporation, Baton rouge, La., USA) supported as described in B were subsequently added as cocatalyst. The solution was stirred at room temperature for 60 minutes. The solvent was then removed in an oil pump vacuum, giving a light-red free-flowing powder.

Comparison:

Dimethylsilanediylbis(2-methyl-4-phenylindenyl)zirconium dichloride/dihydroxyoctafluorobiphenyl 0.30 ml of trimethylaluminum (20% strength in Exxol, 700 µmol) was added to a solution of 50 mg (80 µmol) of dimethylsilanediylbis(2-methyl-4-phenylindenyl)zirconium dichloride in 50 ml of toluene and the solution was stirred at room temperature for 1.5 hours. 1920 µmol/g [$SiO_2$] of cocatalyst (5) were subsequently added. The solution was stirred at room temperature for 60 minutes. The solvent was then removed in an oil pump vacuum, giving a light-red free-flowing powder.

D) Polymerization

For introduction into the polymerization system, the appropriate amount of the supported catalyst system prepared under B (16 μmol of metallocene) was resuspended in 30 ml of Exxol. In parallel thereto, a dry 16 dm³ reactor was flushed firstly with nitrogen and subsequently with propylene and charged with 10 dm³ of liquid propene. 0.5 cm³ of a 20% strength triisobutylaluminum solution in Varsol, diluted with 30 cm³ of Exxol, were then introduced into the reactor and the mixture was stirred at 30° C. for 15 minutes. The catalyst suspension was subsequently introduced into the reactor. The reaction mixture was then heated to the polymerization temperature of 60° C. (4° C./min) and the polymerization system was held at 60° C. for 1 hour by cooling. The polymerization was stopped by venting the remaining propylene. The polymer obtained was dried in a vacuum drying oven. The reactor displayed no deposits on the interior wall or stirrer. The results of the polymerization are summarized in the following table. These results demonstrate that a higher polymerization activity is found when using the chemical products of the present invention as cocatalysts.

| Supported catalyst system prepared using cocatalyst No. | 1 | 2 | 3 | 4 | 5 |
|---|---|---|---|---|---|
| Amount of metallocene [mg] | 50 | 50 | 50 | 50 | 50 |
| Metallocene (μmol) | 80 | 80 | 80 | 80 | 80 |
| Cocatalyst (μmol) | 1920 | 1920 | 1920 | 1920 | 1920 |
| Weight of catalyst system obtained [mg] | 1000 | 1000 | 1000 | 1000 | 1000 |
| Weight of catalyst system used for polymerization [mg] [16 μmol of metallocene] | 200 | 200 | 200 | 200 | 200 |
| Time (min) | 60 | 60 | 60 | 60 | 60 |
| PP (kg) | 0.62 | 0.78 | 0.58 | 0.41 | 0.18 |

We claim:

1. A chemical product suitable as cocatalyst which is obtained by reacting a compound of the formula (I), $$M^1R^1R^2(R^3)_m \quad (I),$$

where
  $R^1$, $R^2$ $R^3$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl,
  $M^1$ is an element of main group II or III of the Periodic Table of the Elements and
  m is 0 or 1, with m being 1 when $M^1$ is an element of main group III and m being 0 when $M^1$ is an element of main group II,
with a compound of the formula (II), $$(R^4X)_q\text{-}(G)^*(M^2R^5R^6)_g \quad (II),$$

in which heteroatom-containing substituents $R^4X$ are located on a parent moiety G, where
  $R^4$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl, or $C_7$–$C_{40}$-haloalkylaryl,
  X is an element of main group VI of the Periodic Table of the Elements,
  G is at least divalent $C_1$–$C_{20}$-haloalkylene, $C_6$–$C_{40}$-haloarylene, $C_7$–$C_{40}$-haloarylene or $C_7$–$C_{40}$-haloarylalkylene,
  $M^2$ is an element of main group IV, of the Periodic Table of the Elements,
  $R^5$, $R^6$ are identical or different and are each hydrogen, $C_1$–$C_{20}$-alkyl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl,
  q is an integer from 2 to 10 and
  g is an integer from 1 to 10.

2. The chemical product as claimed in claim 1, wherein X and $M^2$ are each oxygen and
$R^4$, $R^5$ and $R^6$ are each hydrogen.

3. A process for preparing a chemical product suitable as cocatalyst by reacting a compound of the formula (I), $$M^1R^1R^2(R^3)_m \quad (I),$$

where
  $R^1$, $R^2$ $R^3$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl or $C_7$–$C_{40}$-haloalkylaryl,
  $M^1$ is an element of main group II or III of the Periodic Table of the Elements and
  m is 0 or 1, with m being 1 when $M^1$ is an element of main group III and m being 0 when $M^1$ is an element of main group II,
with a compound of the formula (II), $$(R^4X)_q\text{-}(G)^*(M^2R^5R^6)_g \quad (II),$$

in which heteroatom-containing substituents $R^4X$ are located on a parent moiety G, where
  $R^4$ are identical or different and are each hydrogen, $C_1$–$C_{20}$-alkyl, $C_1$–$C_{20}$-haloalkyl, $C_6$–$C_{20}$-aryl, $C_6$–$C_{20}$-haloaryl, $C_7$–$C_{40}$-arylalkyl, $C_7$–$C_{40}$-haloarylalkyl, $C_7$–$C_{40}$-alkylaryl, $C_7$–$C_{40}$-haloalkylaryl,
  X is an element of main group IV, of the Periodic Table of the Elements,
  G is at least divalent $C_1$–$C_{20}$-haloalkylene, $C_6$–$C_{40}$-haloarylene, $C_7$–$C_{40}$-haloarylene or $C_7$–$C_{40}$-haloarylalkylene,
  $M^2$ is an element of main group IV of the Periodic Table of the Elements,
  $R^5$, $R^6$ are identical or different and are each hydrogen, $C_1$–$C_{20}$-alkyl, $C_1$–$C_{10}$-alkoxy, $C_2$–$C_{10}$-alkenyl, $C_7$–$C_{20}$-arylalkyl, $C_7$–$C_{20}$-alkylaryl, $C_6$–$C_{10}$-aryloxy, $C_1$–$C_{10}$-haloalkyl,
  q is an integer from 2 to 10 and
  g is an integer from 1 to 10.

4. A catalyst system comprising, as cocatalyst, the chemical product as claimed in claim 1 obtained by reacting compounds of the formula (I) with compounds of the formula (II).

5. The catalyst system as claimed in claim 4, comprising
A) at least one organic transition metal compound,
B) optionally, at least one main group alkyl,
C) optionally, at least one support component, and
D) at least one chemical product obtainable by reacting compounds of the formula (I) with compounds of the formula (II).

6. The catalyst system as claimed in claim 5, comprising
A) at least one metallocene, and
B) optionally, at least one Lewis base of the formula (VI), $$M^6R^{21}R^{22}R^{23} \quad (VI),$$

where
- $M^6$ is an element of main group V of the Periodic Table of the Elements,
- $R^{21}$, $R^{22}$ $R^{23}$ are identical or different and are each hydrogen, $C_1$–$C_{20}$-alkyl, $C_1$–$C_{20}$-haloalkyl, $C_6$–$C_{40}$-aryl, $C_6$–$C_{40}$-haloaryl, $C_7$–$C_{40}$-alkylaryl or $C_7$–$C_{40}$-arylalkyl, where two radicals or all three radicals $R^{21}$, $R^{22}$ and $R^{23}$ may be joined to one another via $C_2$–$C_{20}$ units, and at least one radical $R^{21}$, $R^{22}$ or $R^{23}$ is not a hydrogen atom or a linear alkyl chain.

7. A process for preparing a polyolefin by polymerization of one or more olefins in the presence of a catalyst system as claimed in claim 6.

* * * * *